United States Patent
Lee et al.

(10) Patent No.: US 6,235,340 B1
(45) Date of Patent: May 22, 2001

(54) BIOPOLYMER-RESISTANT COATINGS

(75) Inventors: Seok-Won Lee, Cambridge; Paul E. Laibinis, Somerville, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/289,288

(22) Filed: Apr. 9, 1999

Related U.S. Application Data

(60) Provisional application No. 60/081,387, filed on Apr. 10, 1998.

(51) Int. Cl.[7] .............................. A61L 15/50; A61L 27/00; A61L 33/00
(52) U.S. Cl. ........................ 427/2.12; 427/2.24; 427/2.25; 427/2.28; 427/2.3; 427/2.31
(58) Field of Search ................................. 427/2.12, 2.13, 427/2.24, 2.25, 2.28, 2.3, 2.31

(56) References Cited

U.S. PATENT DOCUMENTS

| | | | |
|---|---|---|---|
| 4,534,881 | 8/1985 | Sikes et al. | 252/180 |
| 4,603,006 | 7/1986 | Sikes et al. | 252/180 |
| 4,652,459 | * 3/1987 | Engelhardt | 427/2 |
| 5,015,677 | 5/1991 | Benedict et al. | 524/17 |
| 5,281,267 | 1/1994 | Jones | 106/407 |
| 5,462,990 | 10/1995 | Hubbell et al. | 525/54.1 |
| 5,717,047 | * 2/1998 | Russell et al. | 526/278 |

FOREIGN PATENT DOCUMENTS

| | | |
|---|---|---|
| 0902069A2 | 3/1999 | (AT) . |
| 0 532 273 A1 | 3/1993 | (DE) . |
| 0 770 874 A2 | 5/1997 | (EP) . |
| 1113268 | 5/1968 | (GB) . |
| 2026039 | 1/1980 | (GB) . |
| 04055491 | 2/1992 | (JP) . |

(List continued on next page.)

OTHER PUBLICATIONS

Lee Seok–Won and Laibinis E. Paul., "Protein– resistant Coatings for Glass and Metal Oxide Surfaces Derived from Oligo(ethylene glycol)–terminated alkyltrichlorosilanes", Biomaterials 19 : 1669– 1675, (1998).

Mkrksich M. and Whitesides M. G., "Using Self–Assembled Monolayers to Understand the Interactions Man–made Surfaces With Proteins and Cells", Ann. rev. Biophys. Biomol. Struct. 25 : 55–78 (1996).

Prime L. K. and Whitesides M. G., "Adsorption of Proteins onto surfaces Containing End–Atached Oligo(ethylene oxide): A model System Using Self– Assembl3ed Monolayers", J. Am. Chem. Soc. 115:10714– 10721, (1993).

Ulman Abraham., "Formation and Structure of Self–Assembled monolayers", Chem. rev. 96: 1533–0 1554 (1996)

International Search Report (No date).

Robinson, M. et al., "Slime Films on Antifouling Paints: Control Using Germanium Dioxide", *J. coatings technology*, 58:55–59 (1986).

Robinson, M. et al., "Slime Films on Antifouling Paints, Short Term Indicators of Long–Term Effectiveness", *J. Coatings Technology*, 57:35–41 (1985).

*Primary Examiner*—Shrive Beck
*Assistant Examiner*—Jennifer Kolb
(74) *Attorney, Agent, or Firm*—Dana M. Gordon; Foley, Hoag & Eliot LLP

(57) ABSTRACT

The present invention relates to new biopolymer resistant coatings for materials that come in contact with such molecules in solution. Additionally, the present invention discloses a process for the fabrication of these coatings, under mild and scaleable reaction conditions, from simple, low molecular weight molecular components. Furthermore, the present invention teaches a general conceptual strategy for the design of additional protein resistant coatings.

50 Claims, 6 Drawing Sheets

FOREIGN PATENT DOCUMENTS

| | | |
|---|---|---|
| 06071219 | 3/1992 | (JP) . |
| 07185454 | 7/1995 | (JP) . |
| 09183193 | 12/1995 | (JP) . |
| 10088038 | 9/1996 | (JP) . |
| 10120444 | 5/1998 | (JP) . |
| 11012375 | 1/1999 | (JP) . |
| 11000615 | 6/1999 | (JP) . |
| WO 90/14011 | 11/1990 | (WO) . |
| WO 96/38508 | 12/1996 | (WO) . |
| WO 97/08210 | 3/1997 | (WO) . |
| WO 97/33700 | 9/1997 | (WO) . |
| WO 97/49777 | 12/1997 | (WO) . |

* cited by examiner

Key: (a) $CH_2=CH(CH_2)_9Br$, 50% aqueous NaOH, 100 °C, 24 h (79%); (b) $CH_3COCl$, $(CH_3CH_2)_3N$ in $CH_2CL_2$, overnight, (75%); (c) Pt Catalytst (90%)

BIOPOLYMER-RESISTANT COATINGS

RELATED APPLICATIONS

This application claims the benefit of the filing date of U.S. Provisional Application No. 60/081,387, filed Apr. 10, 1998.

GOVERNMENT FUNDING

Work described herein was supported in part with funding from the Office of Naval Research. The United States Government has certain rights in this invention.

BACKGROUND OF THE INVENTION

The fouling of surfaces that come in contact with proteins in solution, e.g., biological fluids and product streams from biochemical reactors, is a pervasive problem. Transfer of solutions of proteins via pipes is impeded by the non-specific binding of proteinaceous material to the interior walls of the pipes; this binding results in a continual decrease in the cross sectional area of the pipe through which the solution may flow. Foreign objects placed in mammals, e.g., during surgical procedures, accumulate proteinaceous material rapidly. In certain cases, this non-specific fouling can partially, or even completely, undermine the initial positive outcome of a surgical procedure. For example, the gradual accumulation of proteinaceous material in and around a artificial heart valve can result in impaired function of the valve, or even in its failure. Furthermore, the accumulation of proteinaceous material around a stent in a blood vessel can result in partial or complete blockage of that vessel. Contact lenses are rendered opaque over time due to the non-specific adsorption of proteins to their surfaces. The non-specific binding of proteins to surfaces can attenuate the sensitivity of sensors exploited in the qualitative and/or quantitative analysis of test samples. These facts underscore the negative effects of non-specific protein adsorption to various surfaces.

A number of strategies have been developed for suppressing non-specific adhesion of proteins to surfaces. One of these strategies involves the pretreatment of a given surface with a specific protein, or proteins, whose effects on that surface are either minimal, predictable, or both. A second strategy centers on coatings which resist adsorption of proteins by presenting a microscopic surface that lacks the structural characteristics responsible for non-specific adhesion. A tremendous amount of scientific resources has been applied to the design, development, testing and the like of protein-resistant coatings, components thereof, and methods for their application. Advances have been achieved in these areas, but the need remains for further improvements in the state-of-the-art in this field.

SUMMARY OF THE INVENTION

The present invention relates to new biopolymer resistant coatings. Additionally, the present invention discloses a process for the fabrication of these coatings, under mild and scaleable reaction conditions, from simple low molecular weight molecular components. Furthermore, the present invention teaches a general conceptual strategy for the design of additional biopolymer resistant coatings.

DETAILED DESCRIPTION OF THE INVENTION

Figure 1:
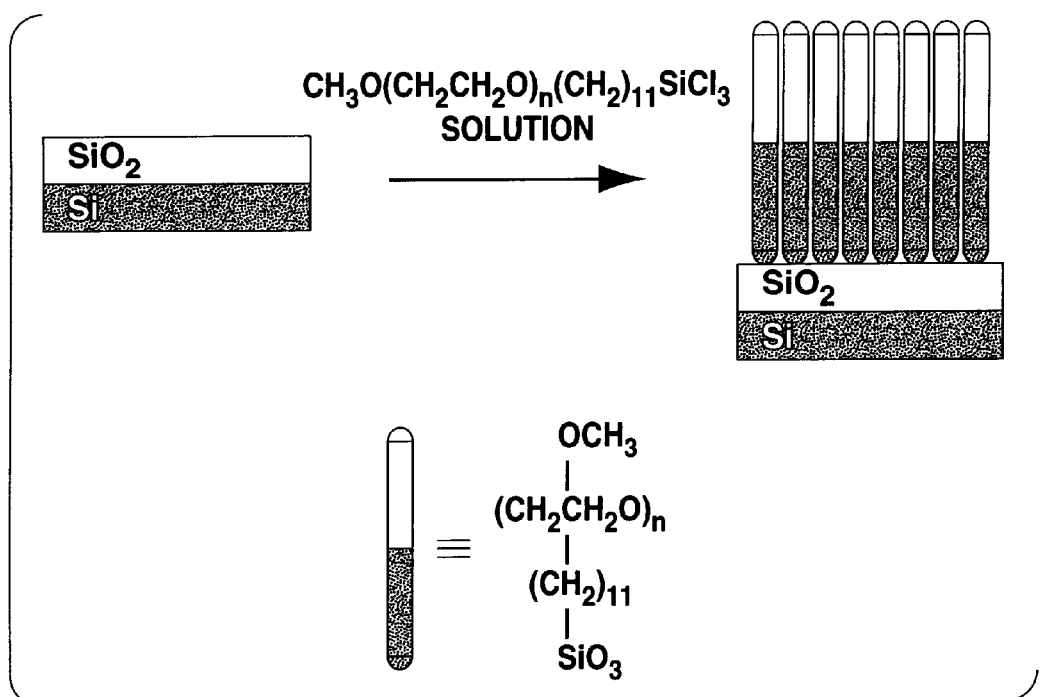
FIG. 1 is a schematic illustration for formation of the oligo(ethylene glycol)-terminated self-assembled monolayers (SAMs).

The immobilization of proteins on both organic and inorganic surfaces is a well-established technique (see, e.g, Chapter 4, Principles of Immobilization of Enzymes, Handbook of Enzyme Biotechnology, Second Edition, Ellis Horwood Limited, 1985), and it is possible to bond a large amount of protein to the surface while retaining adequate biological activity.

However, it has been found that most solid surfaces are so constituted that they adsorb proteins and other biopolymers spontaneously. Such adsorption from aqueous solution is promoted primarily by two types of physical forces, electrostatic attraction, and hydrophobic interaction. Most surfaces, including glass, at normal pH are negatively charged, but usually they also contain hydrophobic domains. A protein usually has positive, negative and hydrophobic seats, which means that a protein is attracted to most surfaces, on the one hand by electrostatic attraction between positive seats and negatively charged groups in the surface, and, on the other hand, by hydrophobic interaction between hydrophobic domains of the protein and the surface. This is described in, for example, Surface and Interfacial Aspects of Biomedical Polymers, Ed. J. D. Andrade, Plenum Press (1985), Vol. 2, p. 81.

Such nonspecific adsorption by electrostatic attraction and hydrophobic interaction is an undesired phenomenon for many applications involving, e.g., the contact of biological fluids or preparation and storage of biopharmacutical products. In solid phase diagnostics, for instance, it results in an impaired sensitivity and a shorter life of the diagnostic kit. In both extracorporeal therapy and in bio-organic synthesis, spontaneous adsorption causes impaired activity and a shorter product life.

I. Overview

One aspect of the present invention relates to a method of significantly reducing the adsorption proteins and other biopolymers on solid oxide surfaces so as to provide the surfaces with a layer of an uncharged hydrophilic polymer, preferably a thoroughly developed hydrophilic surface of low spontaneous adsorption. By coating the surface with a layer of uncharged hydrophilic polymer, such as polyethylene glycol side chains, both electrostatic attraction and hydrophobic interaction can be avoided. The hydrophilic surface does not attract the protein. On the contrary, it acts as a repellent, because it is energetically unfavorable for a protein in aqueous solution to approach such a surface. Thus, the treated surfaces showing such advantageous properties may be described as having improved biocompatability compared to untreated surfaces.

In general, the subject coatings are fabricated by treating an oxide surface, such as glass, with a mixture comprising an excess of a molecule, or molecules, that adhere to the surface and in so doing form the coating. The association between the constituent molecules of the coating and the surface to be coated may be based on hydrophobic interactions, electrostatic interactions, covalent bonds, or a combination of any, or all, of these classes of association.

In addition the present invention offers the further advantages in many applications that the coated surfaces have improved wettability and improved lubricity. This assists in, for instance, avoiding the formation of gas bubbles in tubing and facilitating insertion of catheters via surgical incisions.

The subject method can be applied in such fields as ophthalmologic devices (activation of biochemical process, impaired optical properties); blood bags and related devices for collection and storage of blood and blood components; food processing and storage, including dairy and meat industries; pharmaceutical products (adsorption and denaturation of peptides or other active agents); human hygiene products (such as diapers and sanitary napkins); membranes (polarization and fouling); Sensors (non-specific binding); separation processes, such as chromatography, electrophoresis, and field flow fractionation.

It has also been found that surfaces coated by the process of the present invention possess no net surface charge. Such properties lead the process of the invention to have further applications for instance in the electronics industry and in electrochemical detection and analysis where electrostatic charge or interfering background charge needs to be minimised.

The surface to be treated may be, merely to illustrate, a blood-contacting surface, or it may be some other type of surface, e.g. the surface of a biosensor, bioseparation chamber, or the surface of an electronic device or component or of an electrochemical detection or analysis device. It may be a surface of a finished device such as a blood-contacting device or it may be the surface of a material to be used in forming a finished device. In the latter case subsequent forming steps are selected to avoid disrupting the coating formed by the process of the invention in portions of the device where the coating will protect the surface in use and to avoid chemical damage, for instance due to high temperatures, to the coating. The surface being treated may also be referred to herein as the "substrate".

Such coated surfaces therefore have applications in blood contacting devices and in devices where reduced non-specific protein adsorption is desirable, for instance in diagnostic devices which require a specific interaction of an analyte and detector species, e.g. biosensors, bioseparation membranes and sight correction devices.

In one embodiment, the subject method can be used for improving medical or laboratory devices to increase biocompatibility and resistance to protein binding.

II. Definitions

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry,* McGraw Hill Book Company, New York, (1977 edition) pp. 251–259. The Hammett constant values are a generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl"

have similar chain lengths. Throughout the application, preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

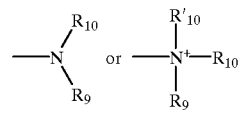

wherein $R_9$, $R_{10}$ and $R'_{10}$ each independently represent a hydrogen, an alkyl, an alkenyl, —$(CH_2)_m$—$R_{80}$, or $R_9$ and $R_{10}$ taken together with the N atom to which they are attached complete a heterocycle having from 4 to 8 atoms in the ring structure; $R_{80}$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_{80}$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

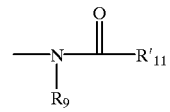

wherein $R_9$ is as defined above, and $R'_{11}$ represents a hydrogen, an alkyl, an alkenyl or —$(CH_2)_m$—$R_{80}$, where m and $R_{80}$ are as defined above.

The term "amido" is art recognized as an amino-substituted carbonyl and includes a moiety that can be represented by the general formula:

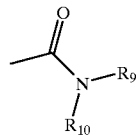

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_{80}$, wherein m and $R_{80}$ are defined above. Representative alkylthio groups include methylthio, ethyl thio, and the like.

The term "carbonyl" is art recognized and includes such moieties as can be represented by the general formula:

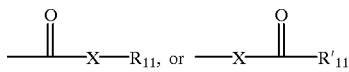

wherein X is a bond or represents an oxygen or a sulfur, and $R_{11}$ represents a hydrogen, an alkyl, an alkenyl, —$(CH_2)_m$—$R_{80}$ or a pharmaceutically acceptable salt, $R'_{11}$ represents a hydrogen, an alkyl, an alkenyl or —$(CH_2)_m$—$R_{80}$, where m and $R_{80}$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$CH_2)_m$—$R_{80}$, where m and $R_{80}$ are described above.

The term "sulfonate" is art recognized and includes a moiety that can be represented by the general formula:

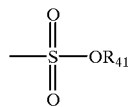

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

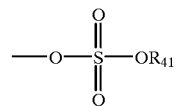

in which $R_{41}$ is as defined above.

The term "sulfonamido" is art recognized and includes a moiety that can be represented by the general formula:

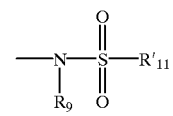

in which $R_9$ and $R'_{11}$ are as defined above.

The term "sulfamoyl" is art-recognized and includes a moiety that can be represented by the general formula:

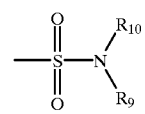

in which $R_9$ and $R_{10}$ are as defined above.

The terms "sulfoxido" or "sulfinyl", as used herein, refers to a moiety that can be represented by the general formula:

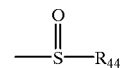

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

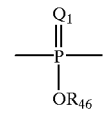

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

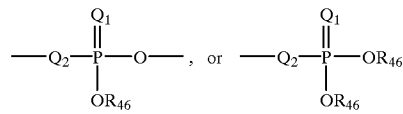

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

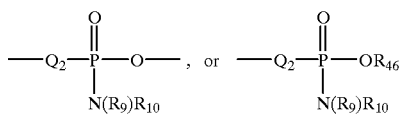

wherein $R_9$ and $R_{10}$ are as defined above, and $Q_2$ represents O, S or N.

A "phosphoramidite" can be represented in the general formula:

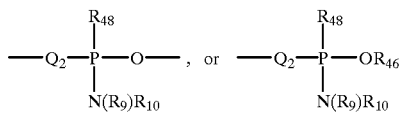

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_{80}$, m and $R_{80}$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by resolution, i.e., derivation with a chiral auxiliary followed by separation of the resulting diastereomeric mixture and cleavage of the auxiliary group to provide the pure enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the properties of the compound. In general, the compounds of the present invention may be prepared by the methods illustrated in the general reaction schemes as, for example, described below, or by modifications thereof, using readily available starting materials, reagents and conventional synthesis procedures.

In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The term "protein-resistant domain" refers generally to hydrophilic, uncharged moieties that render a coated surface resistant to spontaneous association with a biopolymer, e.g., proteins, nucleic acid and/or carbohydrates.

In the context of the present invention, the term biopolymer refers to any polypeptide (such as proteins, enzymes, antibodies, etc.), polysaccharide, or polynucleic acid or conjugate of any of these polymers.

By the term "resistance to biopolymer adsorption" it is meant that the surface has a reduction in the amount of a biopolymer adsorbed on the surface, when contacted with a medium containing biopolymers available for adsorption, as compared to the amount adsorbed on the same surface before treatment by the subject method.

The term "biocompatibility", as used herein to describe the coated surfaces of this invention, refers to the resistance to adsorption of protein and to the lack of interactiveness with physiological surfaces, e.g., as discussed herein.

III. Components and Fabrication of the Coatings

The subject coatings are fabricated by treating a surface with a mixture comprising an excess of a molecule, or molecules, that adhere to the surface and in so doing form the coating. The association between the constituent molecules of the coating and the surface to be coated may be based on hydrophobic interactions, electrostatic interactions, covalent bonds, or a combination of any, or all, of these classes of association.

Protein resistant coatings of the present invention may be applied to myriad surfaces including, but not limited to, surfaces comprising main group elements, alkali and alkaline earth metals, transition metals, and heteroatoms. In certain embodiments, the surface to be coated comprises main group and/or transition metal oxides, main group and/or transition metal sulfides, or main group and/or transition metal nitrides. In preferred embodiments, the surface to be coated comprises —OH, —N(H)—, and/or —SH moieties.

The adhesion of the constituent molecules of the coating to the surface to be coated may be based on hydrophobic interactions, electrostatic interactions, covalent bonds, or a combination of any, or all, of these types of association. For example, in instances of the present invention wherein electrostatic interactions play a role in the adhesion of the coating to the surface, when the surface to be coated includes cationic or anionic moieties, the constituent molecules of the coating comprise anionic or cationic moieties, respectively. In embodiments wherein hydrophobic interactions play a role in the adhesion of the coating to the surface, the surface and the constituent molecules of the coating comprise complementary hydrophobic domains. In embodiments wherein the adhesion of the coating to the surface comprises covalent bonds, the surface comprises moieties, e.g. —OH, —N(H)—, —SH, and the like, which react, to form a covalent bond, with a functional group, e.g. C-halide, Si-halide, transition metal-halide, and the like, of the constituent molecules of the coating. In certain embodiments, the adhesion of the constituent molecules of the coating to the coated surface will comprise more than one point of contact, e.g. hydrophobic interaction, electrostatic interaction, or covalent bond, between an individual component molecule and the surface.

The constituent molecules of the coating comprise a protein-resistant domain, e.g. a hydrophilic substructure or moiety, situated such that said protein-resistant domain is located on, or near, the surface of the coating that will be exposed to the protein-containing sample or solution. The protein resistant domain is selected from the set comprising hydrophilic groups and charged groups that repel the surface charge of a protein. In preferred embodiments, the protein-resistant domain is selected from the set of charge-neutral hydrophilic moieties comprising alcohols, ethers, carbonyls, esters, amides, hydroxamic acids, sulfones, and sulfides.

While not limiting the effectiveness of this invention to any specific theory, the qualities of these coatings are believed to be superior when generated using predominantly or exclusively ethylene oxide-based diols or polyols in the formulation of the prepolymers and hydrated polymers. Representative examples of polyols for forming these precursors include: ethylene glycol, 1,3-propylene glycol, 1,2-propylene glycol, 1,4-butylene glycol, butene-1,4 diol, 1,5-pentane diol, 1,4-pentane diol, 1,6-hexane diol, diethylene glycol, glycerine, trimethylol propane, 1,3,6-hexanetriol, trimethanolamine, pentaerythritol, sorbitol.

The diols and polyols used in the subject method may be made up of ethylene oxide monomer units. Preferably, at least 75% of the units should be ethylene oxide, more preferably at least 90%, and even more preferably at least 95%. Most preferably, substantially all or all of the units should be ethylene oxide.

The biopolymer-resistant coating is formed by treating the surface to be coated with individual molecules represented by general structure 1:

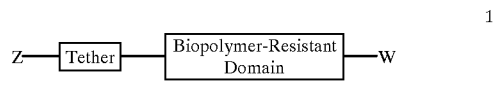

1 wherein

Z represents a domain, moiety, or functional group which associates with the surface to be coated;

tether represents a covalent attachment between Z and the biopolymer-resistant domain;

biopolymer-resistant domain represents a molecular substructure to which biopolymers in solution do not adhere well; and W represents H, a small alkyl group, or a small hydrophilic group.

In preferred embodiments, the biopolymer-resistant coating is formed by treating the surface to be coated with individual molecules represented by general structure 1, wherein:

Z represents a functional group which associates with the surface to be coated selected from the set comprising —$CO_2H$, —$PO_3H_2$, —$C(O)NHOH$, —$Si(OR)_3$, —$SiCl_3$, —$Sn(OR)_3$, —$SnCl_3$, —$Ge(OR)_3$, and —$GeCl_3$;

tether represents a hydrophobic covalent attachment, typically of approximately 5 to 20 bonds in length, between Z and the protein-resistant domain;

biopolymer-resistant domain represents a molecular substructure, to which biopolymers in solution do not adhere well, selected from the set comprising oligoethers, oligoglycols, oligoalcohols, oligocarbonyls, oligosulfides, oligosulfones, and oligosaccharides; and W represents H, a small alkyl group, an alkoxyl group, an acyl group, an acyloxy group, a sulfone, a hydroxyl group, a sulfhydryl group, or a thioalkyl group.

In highly preferred embodiments, the biopolymer-resistant coating is formed by treating the surface to be coated with individual molecules represented by general structure 1, wherein:

Z represents a functional group which associates with the surface to be coated selected from the set comprising —$Si(OR)_3$, —$SiCl_3$, —$Sn(OR)_3$, —$SnCl_3$, —$Ge(OR)_3$, and —$GeCl_3$;

tether represents a hydrophobic covalent attachment, typically of approximately 5 to 20 carbons in length, between Z and the protein-resistant domain;

biopolymer-resistant domain represents a molecular substructure, to which biopolymers in solution do not adhere well, selected from the set comprising oligoethers, oligoglycols, oligoalcohols, oligocarbonyls, oligosulfides, oligosulfones, and oligosaccharides; and W represents H, a small alkyl group, an alkoxyl group, an acyl group, an acyloxy group, a sulfone, a hydroxyl group, a sulfhydryl group, or a thioalkyl group.

A surface bearing a coating of the present invention on a surface may be represented by 2.

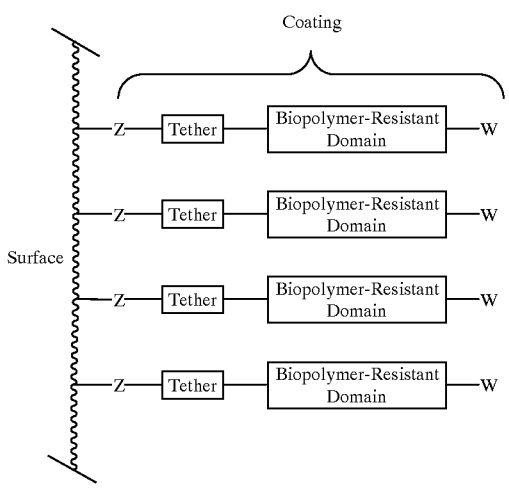

In preferred embodiments, the thickness of the coating will be selected according to the intended use of the device. Typical thicknesses envisaged for coatings according to the invention are in the order of 0.1 to 1000 nanometers, preferably 1 to 100 nanometers and most preferably about 1–10 nanometers.

The coating may may be applied to the substrate by any conventional coating technique such as immersion in a coating bath, spraying, painting or, for flat substrates, spin-coating, the coating conditions being varied according to the desired thickness of coating and the other characteristics of the substrate which will be appreciated by the skilled artisan. Preferably coating is achieved by immersion of the substrate in a bath of the coating at an appropriate concentration and temperature for sufficient time to cover the surfaces to be coated. The solvent may be removed by conventional techniques, preferably by evaporation under reduced or ambient pressure, in a gas stream and/or at elevated temperature. By careful selection of the solvent, concentration of the solution and coating and solvent removal techniques, the thickness of the coating may be controlled within a desired range. Particularly preferred solvents, concentrations and coating and solvent removal techniques are described in detail and illustrated by the Examples.

The coatings of the invention may be applied to a wide variety of laboratory and medical care instruments and devices. The coatings themselves may be, in certain instances, transparent and do not interfere visually with any purpose of the coated substrate. If desired, colorants or other compounds may be added. Moreover, certain of the transparent coatings of this invention may remain transparent and unclouded even after steam sterilization or prolonged exposure to a protein-containing environment. Medical devices may be coated, as may various types of labware which is used in conjunction with tissue or cell cultures, protein-containing fluids such as blood or serum, or the like. This would include as appropriate, but not be limited to, assay plates, supports or membranes, glassware, cell culture or bioreactor devices or assemblies, tubing for blood transfer, blood cell storage bags, filters, pharmaceutical manufacturing and packaging, protein isolation, preparation and purification devices or systems, etc. Any device or apparatus made of glass.

IV. Exemplary Uses of Coatings

In one aspect, it is the object of the present invention to provide a method for modifying the surface of an apparatus or device to create a surface that exhibits resistance to "biomolecule adsorption." In the context of the present invention, the term biomolecule refers to any polypeptide (such as proteins, enzymes, antibodies, etc.), polysaccharide, or polynucleic acid. By the term "resistance to biomolecule adsorption" it is meant that the surface which exhibits a reduction in the amount of a biomolecule adsorbed on the surface, when contacted with a medium containing biomolecules available for adsorption, as compared to the amount of biomolecules adsorbed on the same surface before being coated with the coating composition of this invention.

Broadly, the coating composition of this invention is desireable for the production of all surfaces which will be exposed to environments containing biomolecules and which are desired to exhibit a resistance to deposition by biomolecule adsorption. It is known in the art that all devices which are used in contact with protein-containing fluids or biological fluids must be selected on the basis of acceptable physical and mechanical properties and compatibility with the protein-containing or biological fluids. Examples of these devices or apparatii include glassware and experimental hardware used for conducting experiments. Examples of such glassware include glassware used in protein purification separation, blood bags, pipets, syringes, etc. Also included are containers used for the storage of biologicals and transport of biological material.

Medical devices which come in contact with biological fluids and hence may be coated with the compositions disclosed herein include catheters that are used surgically for insertion through blood vessels, the urethrea, or body conduits, and guidewires used with catheters for biopsy, balloon angioplasty and other medical procedures. As used herein, the term "medical apparatus" means apparatus suited for use in medical applications, particularly in vivo applications. Such apparatus specifically includes, but are not limited to, catheters, balloon catheters, guide wires, endotracheal tubes, implants and other biomedical devices such as, for example, the outer surface of an endoscope. Of particular note for use with the invention are catheters having inflatable balloons such as those developed for use in angioplasty and valvuloplasty, guide catheters and guidewires. Contact lenses are another area requiring biomolecule resistant coatings for preventing deposition of undesirable materials.

For any given application of these materials it is usually difficult to optimise all of these considerations simultaneously and a compromise must be reached often resulting in less than optimal performance. For example, major biological problems are often encountered with materials which have otherwise optimal mechanical and physical properties. These problems often manifest themselves as undesirable deposition of biological components, in particular, proteinaceous material. For instance, protein adsorption results in blood clot formation in blood-contacting materials, the adsorption of tear components onto contact lenses resulting in deposit formation, formation of deposits on intraocular lenses and in separation media resulting in blockage and failure of separation devices. Such effects lead to significant loss in operational performance and often complete rejection and failure of devices.

In the case of medical devices, for example prostheses and components of blood dialysis equipment, it is common practice to employ biocompatible polymers to form at least the surface of the devices to discourage protein adsorption. However, these materials are not perfect and reaction with the living tissues still remains a problem; for example surface-induced thrombosis is still a major difficulty, particularly where large quantities of blood are contacted with a foreign surface such as in artificial lungs and kidneys. Formation of a clot in an artificial organ has a number of adverse or even catastrophic effects including occlusion of the blood pathway in the extracorporeal system, or embolism if the clot breaks off the artificial surface and lodges in a host blood vessel. Dialysis membranes, heart valves, circulatory-assist devices, blood substitutes and artificial lungs all share this problem.

It is known that materials for use as biocompatible coatings should ideally:

(a) be capable of reproducible manufacture as pure materials;
(b) be capable of being coated onto surfaces without being degraded or adversely changed;
(c) have the requisite mechanical and permeability properties required for the specific function of the device for which they are intended;
(d) be sterilisable without adverse changes in, for example, permeability and mechanical or surface properties;
(e) not be damaged or degraded by the biological environment;
(f) not be carcinogenic.

In applications involving direct contact with blood further restrictions exist. Materials should not:

(g) induce significant platelet adhesion;
(h) interfere with the normal clotting mechanism; or
(i) cause any significant damage to the cellular elements or soluble components of the blood.

There have been many attempts to prepare biocompatible, and specifically blood compatible (i.e, haemocompatible), surfaces, which do not activate the blood coagulation process and do not promote thrombus formation. Examples of such attempts include the preparation of negatively charged surfaces, such as by use of anionic polymers or suitably oriented polymers, preparation of surfaces coated with the natural anticoagulant heparin or synthetic heparin analogues, preparation of surfaces with inherently low surface free energy such as by use of silicone rubber, preparation of albumin-coated surfaces, and preparation of surfaces coated with compounds such as some polymethanes which are thought to adsorb albumin preferentially from blood. All of these however have had limitations.

We have now devised new film-forming coating which can be used to coat surfaces. It has been found that this coating may be applied onto a wide variety of surfaces including, polyethylene, PVC, steel, and poly(imide).

This invention also provides a coating composition which when used to coat surfaces, do not swell, to any significant extent, in aqueous environments; in some situations swelling in aqueous environments can reduce the stability of the coatings. The present invention seeks to provide a biocompatible coating which reduces the deposition of proteins and cells at the substrate surface when the coated substrate comes into contact with a protein-containing solution or biological fluid. Additionally, such coatings bind to surfaces with good adhesion and are not removable in the environment in which the coated surfaces are used, e.g. in use as a coating on a blood-contacting surface.

The extent to which a coating composition renders a surface biocompatible may be assessed as a combination of factors such as reduction in the extent to which the surface causes blood platelet activation, protein adsorption, for instance, as judged by absorption of fibrinogen from human plasma.

In other aspects, the invention relates to methods to construct contact lenses using the compositions of the invention, and to methods to prevent protein absorption by providing contact lenses of the claimed compositions.

Additionally, it is apparent that protein resistance is a valuable property in any apparatus or device which comes in contact with the metabolism of the human or animal body. Accordingly, the compositions of the invention are useful in the preparation of materials for catheters or for medical tubing of any kind used to carry body fluids or other fluids into and out of the body, sutures, cannulas, surgical prostheses, vascular grafting materials and materials used for reconstruction such as heart valves. These compositions are also useful for apparatus used to store or administer body fluids such as blood bags.

Accordingly, in another aspect, the invention relates to medical devices constructed of the compositions of the invention. In still another aspect, the invention relates to methods to coat lenses and other medical devices so that they become more protein resistant. Devices and lenses constructed of any polymeric material can be used as substrates for such coating.

Thus, one embodiment of the present invention provides a biocompatible, protein non-adsorptive medical or laboratory device having a polymer coating on at least one surface thereof in which the polymer of said polymer coating is a hydrophilic, biocompatible hydrated polyurea-urethane polymer gel derived from prepolymer units at least 75% of which are oxyethylene-based diols or polyols having molecular weights of about 7000 to about 30,000, said diols or polyols having essentially all of the hydroxyl groups capped with polyisocyanate, said hydrated polymer gel characterized by transparency and by a surface having improved resistance to nonspecific protein adsorption, an formed by reacting said prepolymer units with water.

To further illustrate one embodiment, the present invention relates to the treatment of the surfaces of materials to prevent or inhibit adsorption of protein or reduce thrombogenicity.

Many modern surgical and other medical procedures involve the use of blood-contacting devices, such as surgical implants, prostheses, catheters, drains and extra-corporeal circuitry. Such devices are used and then discarded for hygiene reasons: such devices must therefore be constructed from the most economical materials available, usually polymeric plastics or glass. However as already mentioned glass and most synthetic and natural polymers tend to induce platelet adhesion and activation. Initiation of the clotting cascade follows, leading to blockage of tubing and clogging of other apparatus such as filtration and dialysis membranes and interference with test procedures which, in certain cases, may have disastrous consequences for patients. Moreover in cases where a device is intended to be implanted into a patient and to remain for a prolonged period, such platelet aggregation and clotting must be avoided over a prolonged period as such a reaction can lead to platelet adhesion and clotting, which can have severe, sometimes disastrous, consequences. It is desirable therefore to develop a treatment for such surfaces which reduces and preferably avoids such a reaction.

The present application describes a simple process for reducing the thrombogenicity of blood-contacting surfaces or inhibiting or preventing the non-specific adsorption of protein surfaces which may be used successfully with surfaces. Briefly, the surface is coated with a stable coating, as described herein, so that thrombogenicity or protein adsorption will be avoided over a prolonged period. It is believed that the coatings used in the present invention may be regarded as non-thrombogenic and involving no interference with blood biochemistry rather than as antithrombogenic.

Typical blood contacting devices whose blood contacting surfaces may be coated using the process of the present invention include glass tubing such as found in portions of catheters, for instance central venous catheters, thoracic drain catheters, and angioplasty balloon catheters, glass tubing used in extra-corporeal circuitry such as in heart and/or lung bypasses and entire extra-corporeal circuits such as whole blood oxygenators, cannulae, vascular grafts, sutures, membranes such as those used in blood separation, apheresis and donorpheresis units, gas exchange membranes such as used in whole blood oxygenators, polycarbonate membranes and haemodialysis membranes and membranes used in diagnostic and biosensor devices, biosensors and other devices used in diagnosis such as cuvettes used in blood clotting time determinations, prostheses, artificial hearts and surgical implants.

Problems can also arise from non-specific protein adsorption at the surface of devices used in many applications, such as medical devices. For instance, in many modem diagnostic devices, such as many biosensors, a specific interaction between an analyte and a detector species is relied upon. In such situations non-specific protein adsorption can cause a dramatic loss in sensitivity or even render the device inoperable. As above, the use of the subject coatings can overcome, or at least alleviate, such problems. Thus, other devices which may be treated to reduce non-specific adsorption of proteins including diagnostic devices such as biosensors, bioseparation membranes, sight correction devices such as contact lenses.

Protein adsorption is also recognised as a problem in sight correction devices such as contact lenses. Protein build up on such devices leads to a loss in comfort to the wearer and a deterioration in vision. It is contemplated that the subject method can be used to render the surface of appropriate contact lenses resistant to proteins, and reduce the rate of cloading of the lenses.

In an exemplary embodiment, the subject method is used to coat glass pharmaceutical vials. Briefly, glass vials can be silylated, prior to treatment with the coating solution, to render the surface very hydrophobic, resulting in a layer of silane on which a very stable coating is formed. Silylation can be carried out, e.g., by the addition of a solution (0.1% w/v in chloroform) of monochlorodimethyloctadecylsilane to the vial.

V. Exemplification

The invention now being generally described, it will be more readily understood by reference to the following examples which are included merely for purposes of illustration of certain aspects and embodiments of the present invention, and are not intended to limit the invention.

EXAMPLE 1

This example describes the preparation of oligo(ethylene glycol)-terminated alkyltrichlorosilanes, $Cl_3Si(CH_2)_{11}(OCH_2CH_2)_nOCH_3$ (n=2, 3), and their use in the formation of self-assembled monolayers on an oxide surface. The adsorption of the trichlorosilanes from solution produces densely packed, oriented monolayer films that are 2–3 nm in thickness. The trichlorosilyl group anchors the molecules to the surface, and the resulting film exposes the ethylene glycol units at its surface, as noted by its moderate hydrophilicity ($\theta_a(H_2O) \approx 68°$). The films are robust with stabilities similar to those of other alkylsiloxane coatings. These oligo(ethylene glycol)-terminated silane reagents produce films that notably exhibit resistances against the non-specific adsorption of proteins from solution that are better than for films prepared from octadecyltrichlorosilane. With insulin, lysozyme, albumin, and hexokinase, no adsorption was observed with the oligo(ethylene glycol)-siloxane coatings whereas protein films of approximately a monolayer formed on surfaces treated with octadecyltrichlorosilane. With fibrinogen, complete resistance was not possible with either coating; however, the oligo(ethylene glycol)-siloxane coatings exhibited greater resistance against non-specific adsorption. The oligo(ethylene glycol)-siloxane coatings offer performance advantages over available systems and could easily provide a direct and superior replacement in protocols that presently use silane reagents to generate hydrophobic, "inert" surfaces.

The non-specific adsorption of proteins and other biomolecules onto surfaces is a problem common to biomedical devices, biochemical processing, and biodiagnostics.[1, 2] This problem is particularly acute for objects made of metal or glass as proteins and other species will often adsorb in multilayer quantities onto their corresponding metal oxide surfaces by electrostatic attraction.[3] Common methods to retard the adsorption include the use of alkyltrichlorosilanes (typically $n-C_{18}H_{37}SiCl_3$) to passivate the glass or metal oxide surface with a covalent hydrocarbon film[4] or the attachment or grafting of poly(ethylene glycol) to the surface.[5-7] In the former approach, molecular films from the silane are prepared on the high energy oxide surface to produce a low energy, hydrophobic surface.[8-10] The attached hydrocarbon chains reduce the non-specific adsorption of proteins by screening the electrostatic attraction between the underlying material and charged biomolecules such as proteins; however, the hydrophobic surface—by nature of having a relatively high interfacial free energy ($\gamma_{SL} \approx 50$ mN/m) when contacted with water—will routinely adsorb roughly a monolayer of protein.

Surface-bound poly(ethylene glycol) (PEG) is a common strategy for retarding the non-specific adsorption of proteins and other biological species.[11] Methods for covalently attaching PEG to surfaces include the incorporation of PEG monomers into polymer networks by graft polymerization[12-18] and the direct attachment of PEG chains to surfaces by various coupling reactions.[11] In graft polymerization, the PEG chains are incorporated as segments of a polymer backbone, and the incorporated PEGs can have limited effect on non-specific adsorption depending on the surface density of the PEG chains.[19, 20] The direct attachment of PEG chains to the surface provides a superior method for manipulating surface properties; however, multiple processing steps are often required for coupling the PEG molecules to the substrate.[21, 22] For inorganic substrates, silane reagents are often used to present reactive organic moieties (amines, epoxides, isocyanates, etc.) that provide sites for the covalent attachment of PEG chains. In these procedures, the molecules used for attach PEG chains to these sites frequently include a variety of specialty PEG derivatives[23]— PEG-monoacrylates, PEG-NH$_2$, PEG-CHO, CH$_3$O-PEG, PEG epoxides, star-PEGs, etc.—whose availability and cost can limit the utility of this approach. For these procedures, the effectiveness of the resulting coated surface is related to the surface density of PEG chains as uncoated regions that expose the underlying material often provide sites that undergo non-specific protein adsorption.[24] Objects with complex morphologies offer particular challenges for this method of surface modification due to difficulties in producing uniform, defect-free coatings of PEG. Molecular precursors, such as analogs of $CH_3(CH_2)_{17}SiCl_3$ that produce densely packed films spontaneously onto surfaces from solution with high uniformity of coverage,[10] could offer distinct advantages over present methods if they exposed a PEG-type surface that retarded the non-specific adsorption of proteins.

To address this problem of surface modification, we have developed two new reagents that combine the protocol of use of the trichlorosilane-based adsorbates with the generation of oligo(ethylene glycol)-based surfaces to generate robust coatings for glass and metal oxide substrates that are resistant against the non-specific adsorption of various proteins. These reagents are based on the results of Prime and Whitesides who demonstrated the effectiveness of films formed by the adsorption of $HS(CH_2)_{11}(OCH_2CH_2)_nOR$ (R=H and n=0, 1, 2, 4, and 6; R=$CH_3$ and n=6) onto gold to retard the non-specific adsorption of proteins.[25] Alkanethiols, $HS(CH_2)_mX$, spontaneously assemble onto gold surfaces via sulfur-gold interactions and form oriented, densely packed molecular coatings ("self-assembled monolayers"=SAMs), where the surface properties of the resulting films are controlled by selection of tail group (X).[26] Their observation that only a few ethylene glycol units were required in these oriented assemblies to retard protein adsorption and that methyl-terminated ethylene glycol units were also effective provided the basis for our exploration of thiol compounds that combine these two factors and our development of the oligo(ethylene glycol)-terminated silane reagents. The methyl cap is needed on the ethylene glycol group for generation of a silane-based reagent that could be used on glass and metal oxide substrates as the hydroxyl group of an ethylene glycol cannot be accommodated within a molecule bearing a trichlorosilyl group due to their cross reactivity. In general, trichlorosilane reagents are useful for functionalizing a broader class of substrates (metal oxides)[26] than the thiols (coinage metals such as gold, silver, and copper),[27] and they are widely used in practical applications as they exhibit dramatically superior levels of stability.[4, 26]

In this paper, we demonstrate the effectiveness of methyl-capped di- and triethylene glycol-terminated silane reagents, $CH_3O(CH_2CH_2O)_{2,3}(CH_2)_{11}SiCl_3$, for producing robust molecular films that inhibit the non-specific adsorption of proteins. In particular, we examined proteins with molecular weights from 10,000 to 400,000 Da (insulin, lysozyme, albumin, hexokinase, and fibrinogen). The reagents contained a methyl cap and either two or three ethylene glycol units as their tail group, where these functionalities become localized after assembly of the coating at the outer surface. Our investigation with these two compounds allowed examination of the effects of oligo-ethylene glycol length and their thickness on the properties of the coating; in this study, the thickness of the ethylene glycol portion of the coating was ~10 to 15 Å. The ethylene glycol-terminated silane reagents adsorb onto the surface of an oxide spontaneously from solution and form a coating by methods (FIG. 1) that are directly analogous to those commonly used to hydrophobize glass with alkyltrichlorosilanes $(CH_3(CH_2)_mSiCl_3)$. We compared the adsorptive properties of the hydrocarbon and ethylene glycol-terminated silane-based coatings with various proteins and examined the abilities of films prepared from the ethylene glycol-terminated silane reagents to maintain their non-adsorptive properties after exposure to conditions of elevated temperatures and humidity.

Materials

Reagents were obtained from Aldrich and used as received unless specified otherwise. Octadecyltrichlorosilane was distilled under reduced pressure before use. 10-Undecylenic-1-bromide was obtained from Pfaltz and Bauer (Waterbury, Conn.). Lysozyme (chicken egg white, grade III), albumin (human, fraction V), fibrinogen (bovine, type I-S), hexokinase (bakers yeast) and insulin (bovine pancreas, type III) were obtained from Sigma (St. Louis, Mo.) and used as received. Silicon wafers were test grade and obtained from Silicon Sense (Nashua, N.H.). Gold shot (99.99%) and chromium-coated tungsten filaments were obtained from Americana Precious Metals (East Rutherford, N.J.) and R. D. Mathis Co. (Long Beach, Calif.), respectively. Oligo(ethylene glycol)-undecenes and undecanethiols were synthesized by reported procedures;[25, 28] methyl-capped derivatives were synthesized by direct modifications to these procedures. $^1H$ NMR spectra were obtained on a Bruker 250 MHz spectrometer in $CDCl_3$ and referenced to residual $CHCl_3$ at 7.24 ppm.

Syntheses of Methyl[(1-trichlorosilyl)undec-11-yl] oligo (ethylene glycol)s

Methyl (undec-10-en-1-yl) oligo(ethylene glycol) [$CH_2=CH(CH_2)_9(OCH_2CH_2)_nOCH_3$; n=2 and 3][25] (9.5 mmol), $HSiCl_3$ (28.5 mmol), and t-butyl peroxide (0.14 mmol) were combined under a dry $N_2$ atmosphere in a glove box. The reaction mixture was stirred for 7 h under UV irradiation by a medium pressure Hg lamp[29] and concentrated under reduced pressure to remove excess $HSiCl_3$. The NMR spectrum of the reaction mixture showed quantitative conversion of the olefin to the trichlorosilane. Further purification was performed by vacuum distillation. Methyl[(1-trichlorosilyl)undec-11-yl] di(ethylene glycol): $^1H$ NMR (250 MHz, $CDCl_3$) δ1.2–1.5 (m, 16H), 1.56 (m, 4H), 3.38 (s, 3H), 3.45 (t, 2H), 3.5–3.75 (m, 8H). Methyl[(1-trichlorosilyl)undec-11-yl] tri(ethylene glycol) was prepared by a similar procedure. $^1H$ NMR (250 MHz, $CDCl_3$) δ1.2–1.5 (m, 16H), 1.56 (m, 4H), 3.38 (s, 3H), 3.45 (t, 2H), 3.5–3.75 (m, 12H).

Preparation of Silicon Substrates

Si(100) test wafers were cut into strips of ~1×3 $cm^2$ that were subsequently cleaned by immersion in freshly prepared "piranha" solution of 70% conc. $H_2SO_4$(aq)/30% $H_2O_2$(aq) (v/v) for 0.5 to 1 h at 70° C. (CAUTION: "piranha" solution reacts violently with many organic materials and should be handled with care). The substrates were immediately rinsed with distilled water, dried in a stream of $N_2$, and used within 1 h of cleaning. This process produces a highly wettable, hydrated oxide surface on silicon with similar properties to that for glass.

Formation of Assemblies on $SiO_2$ and Au

The piranha-cleaned silicon substrates were functionalized by immersion in a 2 mM solution of the trichlorosilane in anhydrous toluene. The solutions were prepared and kept in a dry nitrogen atmosphere (glove box). After 6 to 24 h, the substrates were removed from solution and rinsed in 20 mL of $CH_2Cl_2$. The substrates were removed from the glove box, rinsed sequentially with $CHCl_3$ and ethanol to remove any residual organic contaminants, and dried in a stream of $N_2$. Optical constants were measured on the bare substrates by ellipsometry for use in determining thicknesses subsequently of the adsorbed silane films and protein layers. The piranha-cleaned substrates were typically exposed to the air for no more than 15 min before immersion in the silane solution.

Gold substrates were prepared by the sequential evaporation of Cr (100 Å) and Au (1000 Å) onto Si(100) wafers at pressures of ~10$^{-6}$ torr. The wafers were cut into ~1×3 cm$^2$ strips and immersed into ~2 mM solutions of the thiols in absolute ethanol for 24 h at room temperature. These samples were rinsed with ethanol and blown dry with N$_2$ before use.

Protein Adsorption Experiments

The proteins were dissolved at a concentration of 0.25 mg/mL in phosphate buffer saline (PBS) solution (10 mM phosphate buffer, 2.7 mM KCl, and 137 mM NaCl) that was adjusted to pH 7.4 and contained sodium azide (0.2 mg/mL) as a bacteriostat. The coated substrates were immersed in the PBS solutions for 24 h at 20–25° C., rinsed with deionized water (Milli-Q), and dried in a stream of N$_2$. The amount of protein that remained on each substrate after this procedure was determined by ellipsometry. Experiments were also conducted using adsorption times of 3 to 6 h and yielded similar thicknesses as those performed using adsorption times of 24 h. Adsorption times were standardized to 24 h for consistency.

Contact Angle Measurements

Contact angles were measured on a Ramé-Hart goniometer (Ramé-Hart Inc., Mountain Lakes, N.J.) equipped with a video-imaging system. Drops were placed on at least three locations on the surface in the ambient environment and measured on both sides of the drops. Contacting liquid drops were advanced and retreated with an Electrapipette (atrix Technologies, Lowell, Mass.) at approximately 1 µL/s. Angles were measured to ~±1° and were reproducible from sample to sample within ±2°.

Ellipsometric Film-Thickness Measurements

The thicknesses of the films were determined with a Gaertner L116A ellipsometer (Gaertner Scientific Corporation, Chicago, Ill.). For each substrate, measurements were made before and after derivatization with the trichlorosilanes, and after protein adsorption. The thicknesses of the films were determined using a three-phase model and a refractive index of 1.45[30] and have an error of ±2 Å. The use of this value allows direct comparison with data obtained by other groups and provides an accurate relative measure of the amounts of materials adsorbed on the various coatings.

Results and Discussions

Synthesis of Silane Reagents

We prepared the oligo(ethylene glycol)-terminated alkyltrichlorosilanes via a two-step synthesis from commercially available compounds (Scheme I). The monomethyl ether of an oligo(ethylene glycol) was reacted under basic conditions with 11-bromo-undec-1-ene in dimethylformamide (DMF) to yield an 11-oligo(ethylene glycol)undec-1-ene methyl ether in high yield. Separation of the product from excess reagents was easily performed by extraction. The transformation of the resulting olefin to a trichlorosilane by photochemical addition of trichlorosilane (HSiCl$_3$) proceeded quantitatively. In this reaction, excess HSiCl$_3$ served as the solvent and was removed under reduced pressure to yield the product silane in sufficient purity to produce protein resistant coatings although distillation under reduced pressure was used to produce the target silanes as purified compounds. The process for synthesizing the silane reagents (Scheme I) is amenable to scale-up as each reaction could be performed quantitatively and excess reagents were easily separated from the products by extraction and distillation procedures.

Scheme 1
Synthesis of ω-trichlorosilyl-oligo(ethyleneglycol)derivatives(n = 2–3).

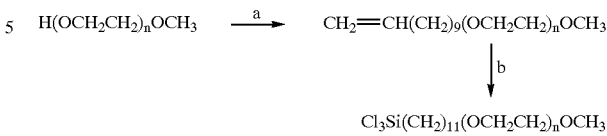

Key:
(a) CH$_2$=CH(CH$_2$)$_9$Br, NaH, THF, reflux, 24 h (80%);
(b) HSiCl$_3$, AIBN, hv, 6 h (90%).

Preparation of Films

Siloxane films were prepared by a straightforward solution-phase adsorption process onto silicon wafers that exposed a hydrated oxide surface (FIG. 1).[26] Silicon was used as a substrate in these studies as its oxide surface is similar to glass in reactivity and its reflective properties allowed measurement of adsorbed protein films by ellipsometry. The semiconducting properties of silicon additionally allowed direct analysis of the surface by x-ray photoelectron spectroscopy to verify formation of the coating and examine the levels of protein adsorption.

To prepare the siloxane coatings, the silicon substrates were immersed into unstirred solutions of the silanes in anhydrous toluene for 6–24 h at room temperature. The silane solutions were handled and stored under a dry N$_2$ atmosphere and yielded reproducible formation of films over several weeks of use. Similar results may be obtained with trichlorosilane-based reagents when the adsorbate solutions are used under ambient laboratory conditions when the relative humidity is less than 40%;[10] however, the compounds exhibit a cumulative sensitivity toward moisture to produce insoluble polymerized aggregates that degrade the properties of the coatings. This problem is common to all trichlorosilane-based reagents (including alkyltrichlorosilanes, CH$_3$(CH$_2$)$_m$SiCl$_3$, used for hydrophobizing glass) due to the hydrolytic instability of the SiCl$_3$ group that is required for film formation. To avoid the possibility of solution-phase hydrolysis and aggregate formation from the silane reagents, we formed the siloxane coatings under a dry atmosphere of nitrogen.

As a comparison to the trichlorosilane-based films, oligo (ethylene glycol)-terminated monolayers on gold were prepared by contacting gold-coated silicon wafers with 2 mM solutions of HS(CH$_2$)$_{11}$(OCH$_2$CH$_2$)$_m$OCH$_3$ (n=0, 2–4) in ethanol for 6–24 h at room temperature. As the assembly of thiols onto gold is not sensitive to humidity, we performed the assembly of these films in the laboratory ambient.

Characterization of the Monolayer Films

Table I displays the wetting properties for films formed upon adsorption of various n-alkanethiols and n-alkyltrichlorosilanes onto Au and Si/SiO$_2$ surfaces, respectively. The wetting properties are compatible with the formation of oriented monolayer films that expose the tail group at the surface, with the thiol and silane-derived films exhibiting similar wetting properties for a common tail group. The formation of monolayer films was confirmed using ellipsometry where thicknesses for the various ethylene glycol-terminated thiols (n=2–4) ranged from 18 to 22 Å and those derived from the methyl-capped di- and triethylene glycol-terminated silanes were 18 and 20 Å, respectively. On gold, we observed that the difference in wettability between the hydroxyl- and methyl-capped ethylene glycol surfaces was ~30° and was much less than the difference for similar substitutions on a purely hydrocarbon chain (~100°). This difference in behavior probably reflects interaction by water with the ethylene glycol framework that moderates that effect of the terminal group. For both systems, water wets the methyl-capped ethylene glycol-terminated films ($\theta_a(H_2O)$=62–72°) better than for the methyl-capped alkyl films ($\theta_a(H_2O)$=110–115°). This greater wettability by the former surfaces implies a lower interfacial energy ($\gamma_{SL}$) between the film and water.

TABLE 1

Contact Angles Measured on Films on Gold and Silicon Obtained from $HS(CH_2)_{11}R$ and $Cl_3Si(CH_2)_{11}R^a$.

| Substrate | $R^b$ | $\theta_a(H_2O)$ | $\theta_r(H_2O)$ |
|---|---|---|---|
| Gold | $CH_3$ | 110 | 99 |
| | $(CH_2)_6CH_3$ | 115 | 99 |
| | OH | 10 | <10 |
| | $(EG)_3OH^c$ | 34 | 23 |
| | $(EG)_4OH^c$ | 38 | 24 |
| | $OCH_3$ | 81 | 68 |
| | $(EG)_2OCH_3$ | 68 | 59 |
| | $(EG)_3OCH_3$ | 62 | 52 |
| | $(EG)_4OCH_3$ | 62 | 52 |
| Silicon | $(CH_2)_6CH_3$ | 115 | 98 |
| | $(EG)_2OCH_3$ | 72 | 55 |
| | $(EG)_3OCH_3$ | 67 | 49 |

$^a$Advancing ($\theta_a$) and receding ($\theta_r$) static contact angles of water.
$^b$EG = —$OCH_2CH_2$—
$^c$Reference 28.

Protein Repellency of Films

We examined the adsorption properties of the methyl-capped oligo(ethylene glycol)-terminated films on Au and $Si/SiO_2$ by immersing them into various protein-containing solutions at a concentration of 0.25 mg/mL for 24 h at room temperature. We performed concurrent experiments in these solutions using surfaces coated with octadecyl chains to allow direct comparisons of the performance of these films with available systems. The amount of adsorbed protein was determined optically ex situ using ellipsometry. We also used techniques such as x-ray photoelectron spectroscopy (for siloxane and thiolate SAMs) and polarized infrared external reflectance spectroscopy (for thiolate SAMs) to determine the amount of adsorbed proteins. These techniques are superior to ellipsometry because on their detection of specific chemical signals—nitrogen composition or amide content—resulting from the protein; however, they required much longer times for characterizing each sample. In general, we found that the thickness data from ellipsometry agreed with results from these other methods, and we used it as our primary characterization method.

Figure 2:
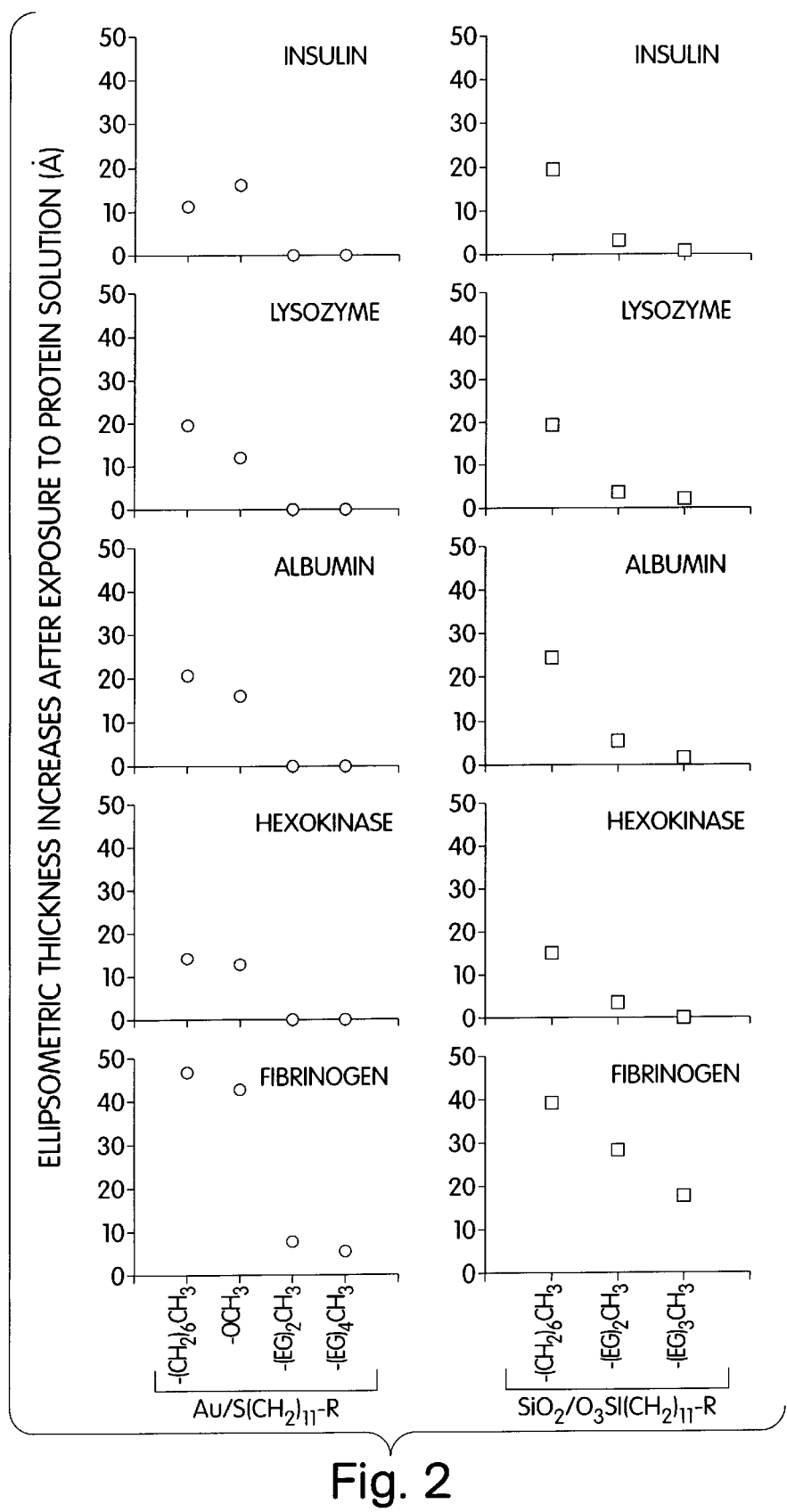
FIG. 2 graphically depicts the ellipsometric thickness of adsorbed films of insulin, lysozyme, albumin, hexokinase, and fibrinogen on various SAM surfaces. EG represents an ethylene glycol unit.
Figure 3:
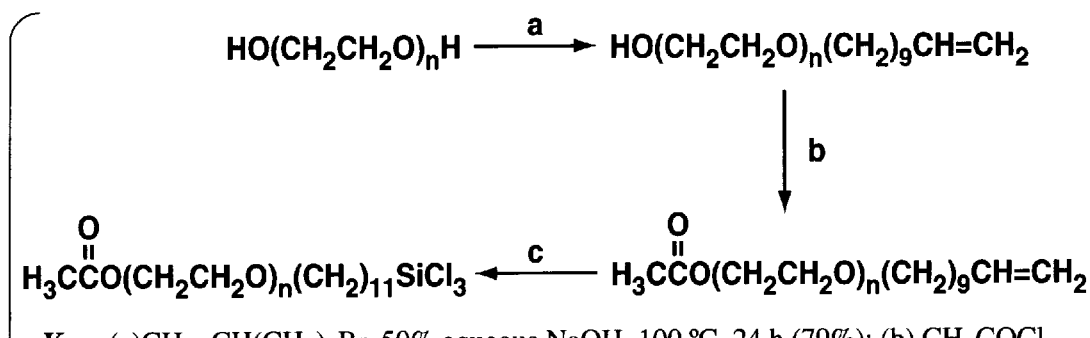
FIG. 3 depicts the synthesis of co-trichlorosilyl-oligo (ethylene glycol) derivatives, $CH_3COO(CH_2CH_2O)_n(CH_2)_{11}SiCl_3(n=3–4)$.
Figure 4:
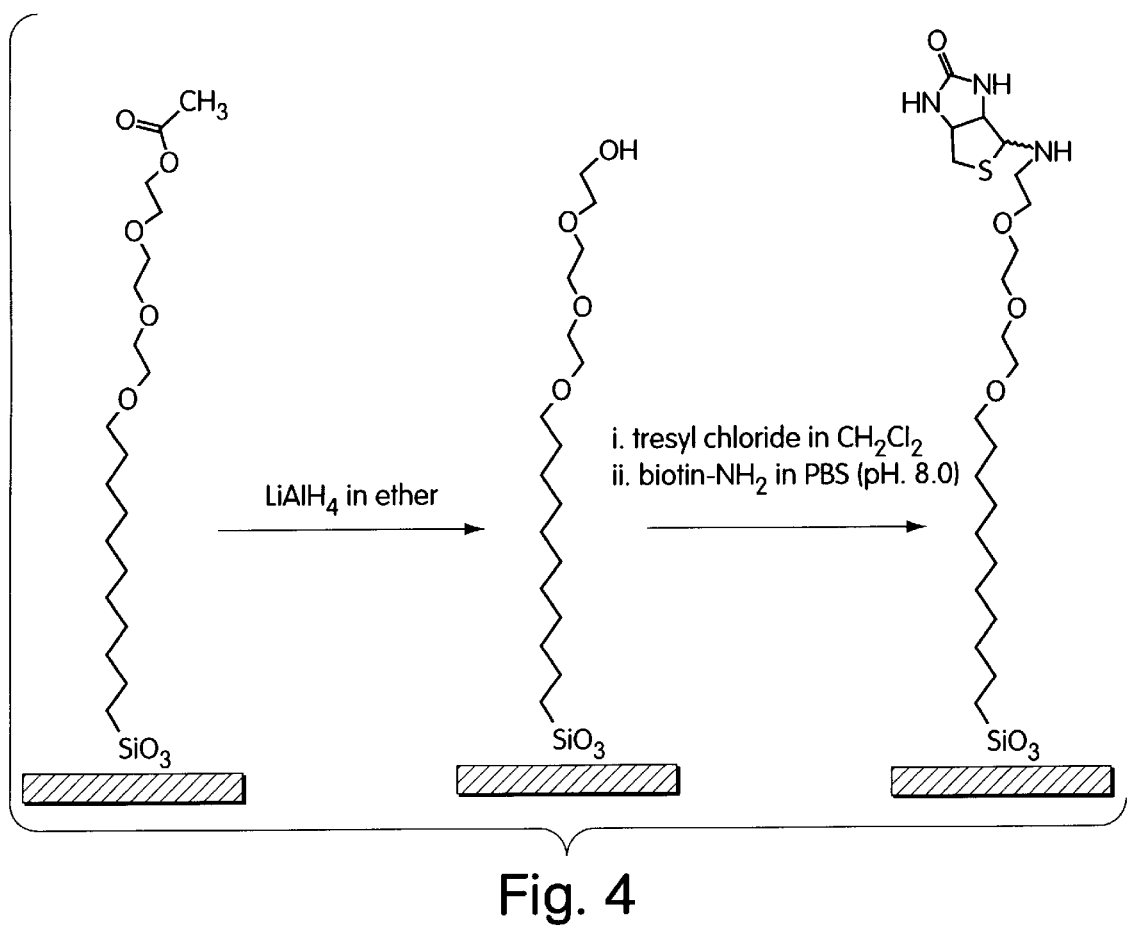
FIG. 4 depicts a schematic representation of on-surface reactions.
Figure 5A:
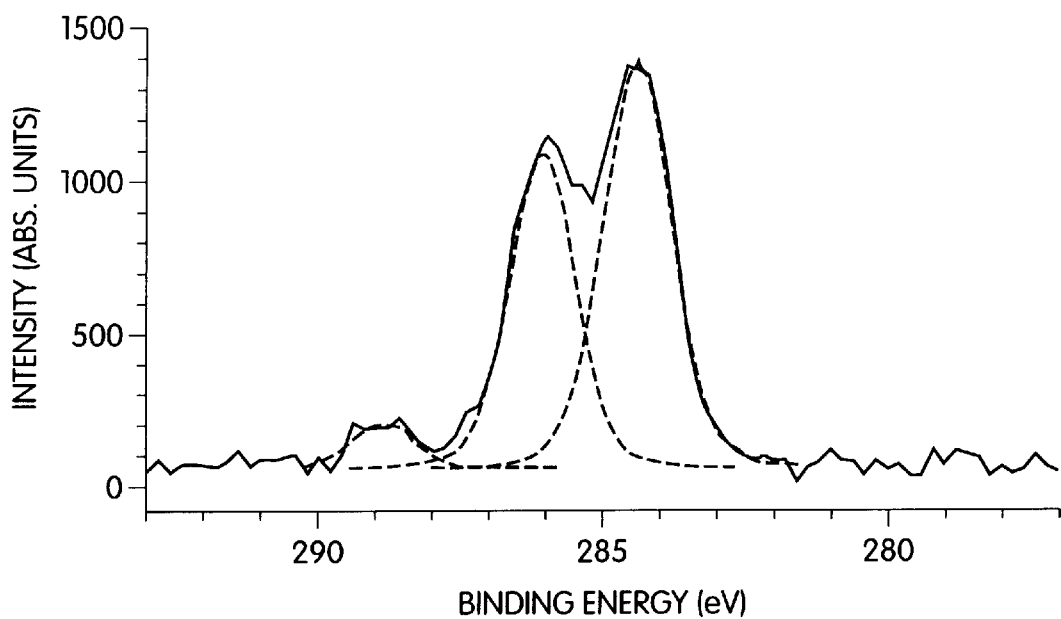
FIG. 5 depicts XPS spectra of acetate- and hydroxyl-terminated EG siloxane SAMs on a $SiO_2$-covered silicon substrate (top and bottom, respectively).
Figure 5B:
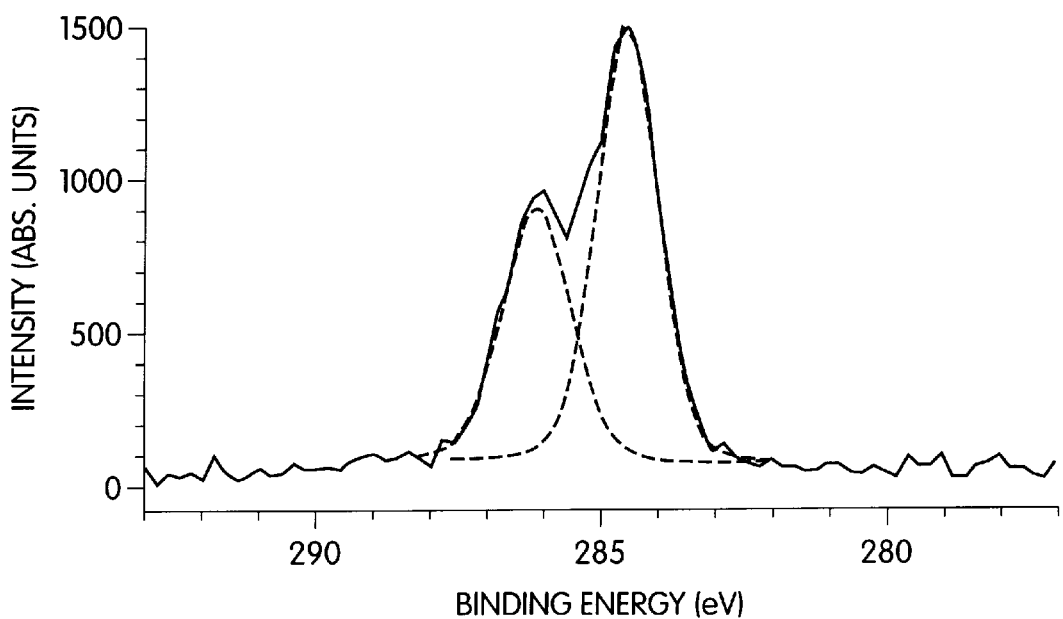
Figure 6:
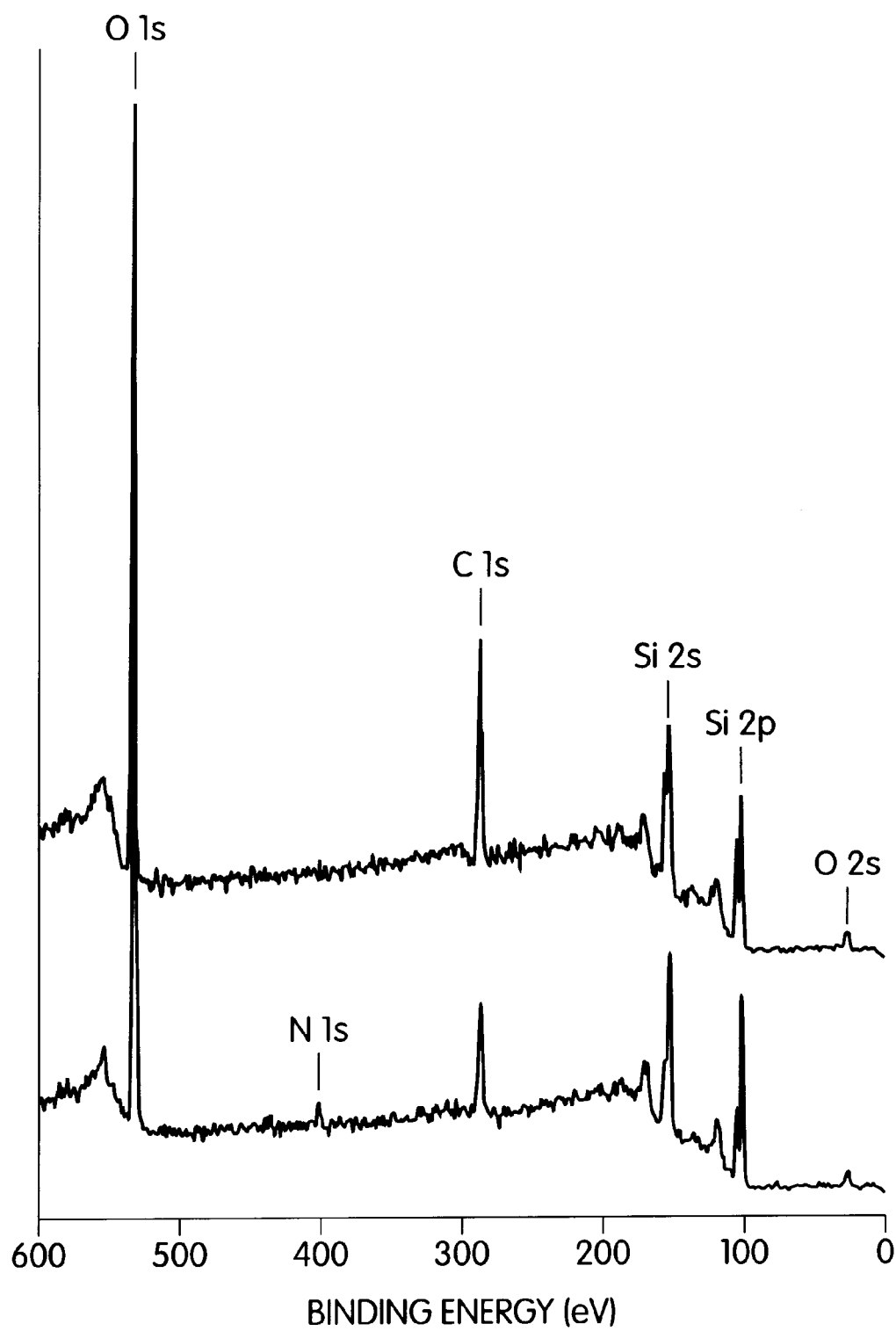
FIG. 6 depicts XPS survey spectra of a hydroxyl-terminated EG SAM before (upper) and after (lower) attachment of biotin.

FIG. 2 summarizes the protein adsorption results for both substrates. On gold, the five proteins adsorbed onto the hydrophobic surfaces prepared from octadecanethiol, with the higher molecular weight proteins forming thicker adsorbed films. These thicknesses correspond to roughly a monolayer of adsorbed protein suggesting that the proteins adsorb to lower the interfacial energy between the hydrocarbon coating and water and the resulting protein surface does not promote further adsorption. A surface expressing a methoxy group (—$OCH_3$) exhibits a lower surface energy than the purely alkyl surface (as evidenced by its lower contact angle by water, Table I); however, this difference did not have a large effect on protein adsorption. This observation suggests that the interfacial free energy for this surface when contacted with water is sufficient to drive adsorption of a layer of protein. Again, roughly a monolayer of protein appears to adsorb suggesting that the protein surface does not promote further protein adsorption.

The incorporation of two and four oligo(ethylene glycol) units as linkers between the methoxy terminus and the alkyl chain resulted in a reduction in the amount of protein adsorption onto the gold surface (FIG. 2). For insulin, lysozyme, albumin, and hexokinase, the SAMs resisted protein adsorption within the experimental errors of ellipsometry. Complete resistance against the adsorption of fibrinogen was not possible with the $EG_{2,4}$—$CH_3$ surface; however, the SAM reduced the adsorbed amount to roughly 10% of a monolayer. The difference in the adsorption characteristics of the purely alkyl $CH_3O$-capped monolayer and the EG-containing $CH_3$-capped film can be explained partially by the lower interfacial energy of the latter system with water. Entropic effects may also be operative for the oligo(ethylene glycol) system.[1, 24]

With the silane reagents, the results mirrored those on the gold substrates where the $CH_3$-capped oligo(ethylene glycol) monolayers adsorbed less protein than did the purely alkyl film. Films derived from octadecyltrichlorosilane adsorbed roughly a monolayer of protein. The $CH_3$-capped di- and tri-(ethylene glycol) films exhibited a resistance against adsorption by insulin, lysozyme, albumin, and hexokinase, with the tri-(ethylene glycol) films offering superior properties and being resistant against adsorption for these proteins within the error of ellipsometry. As for gold, the $CH_3$-capped oligo-(ethylene glycol) films adsorbed fibrinogen, with the adsorbed amounts being greater for the silane-based films than for the thiols on gold. The superior properties on gold may reflect the greater ease for forming oriented, well-defined, self-assembled, thiol-based monolayer films as silane reagents can form polymeric aggregates that can diminish the surface properties of the film.[26] The presence of such aggregates could provide local hydrophobic sites for the adsorption of proteins. As we assembled the silane films under an inert atmosphere and used physical methods to displace any physisorbed materials from the surface, the amount of physisorbed material on our surfaces should be low. Structural differences in the molecular conformation of the $CH_3$-capped tri(ethylene glycol) layer—crystalline vs. amorphous—have been reported to affect the protein resistance of such surfaces toward fibrinogen and such differences may be operative here.[31]

In addition to the ellipsometric results, the wetting properties of the surfaces provided a macroscopic (albeit qualitative) indicator of protein adsorption. The initially prepared surfaces were hydrophobic and emerged dry when rinsed with water. After exposure to the protein solutions, the purely alkyl systems became less hydrophobic, while the oligo(ethylene glycol) surfaces maintained their hydrophobicity. In particular, the receding contact angle of water on surfaces with an adsorbed layer of protein was ~25° and was sufficiently low to provide a visual indication of protein adsorption.

Stability of Films

The practical utility of a coating is based on both its performance and its ability to maintain its useful properties. We examined the stability of the siloxane films by exposing them to various conditions including boiling water, hot hydrocarbon solutions, oven drying, and autoclaving. The films retained their protein resistant properties after immersion in boiling water at 100° C. or decahydronaphthalene (DHN) at 90° C. for 1 h and drying in an oven at 120° C. for 1 h; however, they exhibited significant deterioration after drying in an oven at 200° C. for 1 h. These observations are compatible with the literature regarding the thermal stabilities of siloxane monolayer films as such films are reported to exhibit no detectable changes in structure and wetting properties when heated to ~140° C. and subsequently characterized at room temperature.[9, 32] For our reagents and coatings, the presence of the $CH_3$-capped oligo(ethylene glycol) tail does not appear to negatively impact the thermal stability of an alkylsiloxane monolayer. For use in applications that require sterilized glassware, we note the silane-based coatings maintained their integrity and properties after an extended sterilization cycle (1 h) in an autoclave at ~120° C. (pressure=20 psi). This ability may make these films suitable for numerous applications where sterile conditions are required and there is a need to limit the non-specific adsorption of proteins.

The thermal stabilities of the siloxane monolayers contrasts with the rapid desorption under these conditions for their thiol counterparts on gold. For comparison, ~30% of a thiol-based oligo(ethylene glycol)-terminated monolayer desorbed within 5 min in boiling water and within 1 min in DHN at 90° C. and lost their abilities to resist the non-specific adsorption of proteins, while the siloxane films were stable for at least an hour under these conditions. The robust behavior of the siloxane monolayers offers the needed stabilities required for practical application, with the developed $CH_3$-capped oligo-(ethylene glycol)-terminated silane reagents providing easy access to robust, protein resistant molecular coatings for glass and metal oxide surfaces.

CONCLUSIONS

Molecular coatings that exhibit a resistance against the non-specific adsorption of proteins such as insulin, lysozyme, albumin, and hexokinase can be readily prepared on metal oxide surfaces using a $CH_3$-capped oligo-(ethylene glycol)-terminated silane reagent, $CH_3[OCH_2CH_2]_{2,3}O(CH_2)_{11}SiCl_3$. These compounds are synthesized by a straightforward two-step reaction sequence using commercially available precursors. Solution-phase contact between a metal oxide surface and the silane reagent results in the spontaneous formation of a densely packed, oriented siloxane coating that expresses the oligo(ethylene glycol) groups at its surface. These moderately hydrophilic surfaces exhibit superior protein resistant properties than the more hydrophobic surfaces prepared from the adsorption of octadecyltrichlorosilane onto glass. The oligo-(ethylene glycol)-terminated films maintain their integrity and protein resistant properties after exposure to temperatures of ~100° C. (including sterilization procedures in an autoclave), suggesting that the parent reagents could be suitable for producing coatings on various glassware and another implements that contact protein-containing media and may be exposed to the conditions used in sterilization procedures.

REFERENCES FOR EXAMPLE 1

1. Norde, W., Adsorption of Proteins From Solution at the Solid-Liquid Interface, *Adv. Colloid Interface Sci.* 1986, 25, 267–340.
2. Andrade, J. D. and Hlady, V., Protein Adsorption and Materials Biocompatibility, *Adv. Polym. Sci.* 1986, 79, 1–63.
3. Vroman, L., *Blood,* Natural History Press, 1966.
4. Plueddemann, E. P., *Silane Coupling Agents,* Plenum Press, New York, 1982.
5. Nashabeh, W. and Rassi, Z. E., Capillary Zone Electrophoresis of Proteins with Hydrophilic Fused-silica Capillaries, *J. of Chrom.* 1991, 559, 367–383.
6. Herren, B. J., Shafer, S. G., Van Alstine, J., Harris, J. M. and Snyder, R. S., Control of Electroosmosis in Coated Quartz Capillaries, *J. Colloid Interface Sci.* 1987, 115, 46–55.
7. Yang, Z. and Yu, H., Preserving a Globular Protein Shape on Glass Slides: A Self-Assembled Monolayer Approach, *Adv. Mater.* 1997, 9, 426–429.
8. Maoz, R. and Sagiv, J., On the Formation and Structure of Self-Assembling Monolayers I. A Comparative ATR-Wettability Study of Langmuir-Blodgett and Adsorbed Films on Flat Substrates and Glass Microbeads, *J. Colloid Interface Sci.* 1984, 100, 465–496.
9. Cohen, S. R., Naaman, R. and Sagiv, J., Thermally Induced Disorder in Organized Organic Monolayers on Solid Substrates, *J. Phys. Chem.* 1986, 90, 3054–3056.
10. Wasserman, S. R., Tao, Y.-T. and Whitesides, G. M., Structure and Reactivity of Alkylsiloxane Monolayers Formed by Reaction of Alkyltrichlorosilanes on Silicon Substrates, *Langmuir* 1989, 5, 1074–1087.
11. Harris, J. M., *Poly(Ethylene Glycol) Chemistry,* Plenum Press, New York, 1992.
12. Mori, Y., Nagaoka, S., Takuichi, T., et al., A New Antithrombogenic Material with Long Polyethylene Oxide Chains, *Trans. Am. Soc. Artif. Intern. Org.* 1982, 28, 459–463.
13. Merrill, E. W. and Salzman, E. W., Polyethylene Oxide as a Biomaterial, *Am. Soc. Artif Intern. Org. J.* 1983, 6, 60–64.
14. Sun, Y. H., Gomboltz, W. R. and Hoffman, A. S., Synthesis and Characterization of Non-fouling Polymer Surfaces: I. Radiation Grafting of Hydroxyethyl Methacrylate and Polyethylene Glycol onto Silastic Film, *Compat. Polym.* 1986, 1, 316–334.
15. Grasel, T. G. and Cooper, S. L., Surface Properties and Blood Compatibility of Polyurethaneureas, *Biomaterials* 1986, 7, 315–328.
16. Su, Y. H., S., H. A. and Gomboltz, W. R., Non-fouling Biomaterial Surfaces: II. Protein Adsorption on Radiation Grafted Polyethylene Glycol Methacrylate Copolymers, *Polym. Prep.* 1987, 28, 292–294.
17. Grainger, D. W., Nojiri, C., Okano, T. and Kim, S. W., In vitro and ex vitro Platelet Interactions with Hydrophilic-hydrophobic Poly(ethylene oxide)-heparin Block Copolymers. I. Synthesis and characterization, *J. Biomed. Mater. Res.* 1988, 22, 231–249.
18. Grainger, D. W., Knutsen, K., Okano, T. and Feijin, J., Poly(dimethyl siloxane)-Poly(ethylene oxide)-heparin Block Copolymers. II. Surface characterization and in vitro assessments, *J. Biomed. Mater. Res.* 1990, 24, 403–431.
19. Jeon, S. I. and Andrade, J. D., Protein-Surface Interactions in the Presence of Polyethylene Oxide II. Effect of Protein Size, *J. Colloid Interface Sci.* 1991, 142, 159–166.
20. Jeon, S. I., Lee, J. H., Andrade, J. D. and De Gennes, P. G., Protein-Surface Interactions in the Presence of Polyethylene Oxide I. Simplified Theory, *J. Colloid Interface Sci.* 1991, 142, 149–158.
21. Lassen, B., Gölander, C.-G., Johansson, A. and Elwing, H., Some Model Surfaces Made by RF Plasma Aimed for the Study of Biocompatibility, *Clin. Mater.* 1992, 11, 99–103.
22. Kiss, E. and Gölander, C.-G., Chemical Derivatization of Muscovite Mica Surfaces, *Colloids and Surfaces* 1990, 49, 335–342.
23. Harris, J. M., Laboratory Synthesis of Polyethylene Glycol Derivatives, *Rev. Macromol. Chem. Phys.* 1985, C25, 325–373.
24. Andrade, J. D., Hlady, V. and Jeon, S.-I., Poly(ethylene oxide) and Protein Resistance, in *Hydrophilic Polymers: Performance with Environmental Acceptance,* (Ed. J. E. Glass), American Chemical Society, 1996, 51–59.
25. Prime, K. L. and Whitesides, G. M., Adsorption of Proteins onto Surfaces Containing End-Attached Oligo (ethylene oxide): A Model System Using Self-Assembled Monolayers, *J. Am. Chem. Soc.* 1993, 115, 10714–10721.

26. Ulman, A., *An Introduction to Ultrathin Organic Films: From Langmuir-Blodgett to Self-Assembly,* Academic Press, Boston, 1991.
27. Laibinis, P. E. and Whitesides, G. M., ω-Terminated Alkanethiolate Monolayers on Surfaces of Copper, Silver and Gold Have Similar Wettabilities, *J. Am. Chem. Soc.* 1992, 114, 1990–1995.
28. Pale-Grosdemange, C., Simon, E. S., Prime, K. L. and Whitesides, G. M., Formation of Self-Assembled Monolayers by Chemisorption of Derivatives of Oligo(ethylene glycol) of Structure $HS(CH_2)_{11}(OCH_2CH_2)_mOH$ on Gold, *J. Am. Chem. Soc.* 1991, 113, 12–20.
29. Eabom, C., Harrison, M. R. and Walton, M. R., Catalysis of Hydrosilylation of Olefins by tert-Butyl Peroxide under UV Irradiation, *J. Organomet. Chem.* 1971, 31, 43–46.
30. Allara, D. L. and Nuzzo, R. G., Spontaneously Organized Molecular Assemblies. 2. Quantitative Infrared Spectroscopic Determination of Equilibrium Structures of Solution-Adsorbed n-Alkanoic Acids on an Oxidized Aluminum Surface, *Langmuir* 1985, 1, 52–66.
31. Harder, P., Grunze, M., Dahint, R., Whitesides, G. M. and Laibinis, P. E., Molecular Conformation in Oligo (ethylene glycol)-Terminated Self-Assembled Monolayers on Gold and Silver Surfaces Determines Their Ability to Resist Protein Adsorption, *J. Phys. Chem. B,* in press.
32. Calistri-Yeh, M., Kramer, E. J., Sharma, R., et al., Thermal Stability of Self-Assembled Monolayers from Alkylchlorosilanes, *Langmuir* 1996, 12, 2747–2755.

EXAMPLE 2

Preparation of Biotin-bearing SAMs and Measurements Thereon

Materials

Reagents were obtained from Aldrich and used as received unless specified otherwise. Octadecyltrichlorosilane was distilled under reduced pressure before use. 10-Undecylenic-1-bromide and 5-(biotinamido)pentylamine was obtained from Pfaltz and Bauer (Waterbury, Conn.) and PIERCE (Rockford, Ill.), respectively. Silicon wafers were test grade and obtained from Silicon Sense (Nashua, N.H.). The methyl-capped tri(ethylene glycol)-terminated undecyl-trichlorosilane $(CH_3O(CH_2CH_2O)_3(CH_2)_{11}SiCl_3)$ was available from the previous study. The acetate-capped tri (ethylene glycol)-terminated undecyltrichlorosilane was synthesized by the procedure outlined in Scheme I. We protected the hydroxyl group as acetate to prevent reaction of free hydroxyl groups with chlorosilane groups. $^1$H NMR spectra were obtained on a Bruker 250 MHz spectrometer in $CDCl_3$ and referenced to residual $CHCl_3$ at 7.24 ppm.

Synthesis of Acetyl[(1-trichlorosilyl)undec-11-yl] tri (ethylene glycol)

The acetyl (undec-10-1-yl) tri(ethylene glycol) precursor [1, $CH_2$=$CH(CH_2)_9(OCH_2CH_2)_3OCOCH_3$] was prepared by reported procedures[1,2] and hydrosilated to add a trichlorosilyl group.[3] The NMR spectrum of the reaction mixture showed the quantitative conversion of the olefin to the trichlorosilane by UV. The excess $HSiCl_3$ was removed by vacuum distillation. Acetyl[(1-trichlorosilyl)undec-11-yl ] tri(ethylene glycol): $^1$H NMR (250 MHz, $CDCl_3$, δ): 1.2–1.5 (m, 16H), 1.55 (m, 4H), 2.06 (s, 3H), 3.43 (t, 2H), 3.5–3.75 (m, 10H), 4.20 (t, 2H).

Preparation of $SiO_2$ Substrates

Si(100) test wafers and glass slides were cut into strips of ~1×3 $cm^2$ that were subsequently cleaned by immersion in freshly prepared "piranha" solution of 70% conc. $H_2SO_4$ (aq)/30% $H_2O_2$(aq) (v/v) for 0.5 to 1 h at 70° C. (CAUTION: "piranha" solution reacts violently with many organic materials and should be handled with care). The substrates were immediately rinsed with distilled water, dried in a stream of $N_2$, and used within 1 h of cleaning. This process produces a highly wettable, hydrated oxide surface on silicon with similar properties to that for glass.[4] Optical constants were measured on the bare substrates by ellipsometry for use in determining thicknesses subsequently of the adsorbed silane films and protein layers. The piranha-cleaned substrates were typically exposed to the air for no more than 15 min before immersion in the silane solution.

Formation of Siloxane Films on $SiO_2$

The piranha-cleaned silicon substrates were functionalized by immersion in a ~2 mM solution of the trichlorosilane in anhydrous toluene. The solutions were prepared and kept in a dry nitrogen atmosphere (glove box). After 6 to 24 h, the substrates were removed from solution and rinsed in 20 mL of $CH_2Cl_2$. The substrates were removed from the glove box, rinsed sequentially with $CHCl_3$ and ethanol to remove any residual organic contaminants, and dried in a stream of $N_2$.

Covalent Attachment of Biotin onto SAMs

The silanated substrates were sonicated in 0.1 mM $LiAlH_4$ in anhydrous diethyl ether for 10 mins to convert terminal acetate groups to hydroxyl groups. The substrates were then washed sequentially in ~4% HCl, chloroform, acetone, and deionized water and dried under a stream of $N_2$. The substrates were then tresylated by immersion to a 1.25 mg/mL tresyl chloride solution in $CH_2Cl_2$ for 1 hr at room temperature, rinsed with anhydrous methanol, and dried under a stream of $N_2$.[5] The tresylated samples were then immediately transferred to a 1 mg/mL 5-(biotinamido) pentylamine solution in phosphate buffer saline (PBS) solution (10 mM phosphate buffer, 2.7 mM KCl, and 137 mM NaCl) that was adjusted to pH 8.0.[5]

Contact Angle Measurements

Contact angles were measured on a Ramé-Hart goniometer (Ramé-Hart Inc., Mountain Lakes, N.J.) equipped with a video-imaging system. Drops were placed on at least three locations on the surface in the ambient environment and measured on both sides of the drops. Contacting liquid drops were advanced and retreated with an Electrapipette (Matrix Technologies, Lowell, Mass.) at approximately 1 μL/s. Angles were measured to ~±1° and were reproducible from sample to sample within ±2°.

Ellipsometric Film-Thickness Measurements

The thicknesses of the films were determined with a Gaertner L116A ellipsometer (Gaertner Scientific Corporation, Chicago, Ill.). For each substrate, measurements were made before and after derivatization with the trichlorosilanes, and after protein adsorption. The thicknesses of the films were determined using a three-phase model and a refractive index of 1.45 and have an error of ±2 Å. The use of this value allows direct comparison with data obtained by other groups and provides an accurate relative measure of the amounts of materials adsorbed on the various coatings.

X-ray Photoelectron Spectroscopy (XPS)

The XPS spectra were obtained with a surface Science Instrument Model X-100 spectrometer using a monochromatized Al Kα x-ray source (elliptical spot of 1.0 mm×1.7 mm) and a concentric hemispherical analyzer. The detector angle with respect to the surface parallel was 35°. The step width and pass energy were set at 0.1 and 23 eV, respectively, giving an experimental resolution of ~1 eV. Peak positions were referenced to C(1s)=284.6 eV, and peaks were fit with 80% Gaussian/20% Lorentzian profiles and a Shirley background.

REFERENCES FOR EXAMPLE 2

(1) Pale-Grosdemange, C.; Simon, E. S.; Prime, K. L.; Whitesides, G. M. *J. Am. Chem. Soc.* 1991, 113, 12–20.

(2) Wenzler, L. A.; Moyes, G. L.; Raikar, G. N.; Hansen, R. L.; Harris, J. M.; Beebe Jr., T. P. *Langmuir* 1997, 13, 3761–3768.
(3) Balachander, N.; Sukenik, C. *Langmuir* 1990, 6, 1621–1627.
(4) Pintchovski, F.; Price, J. B.; Tobin, P. J.; Peavey, J.; Kobold, K. *J. Electrochem. Soc.* 1979, 126, 1428–1430.
(5) Liu, S. Q.; Liu, L. S.; Ohno, T. *Cytotechnology* 1997, 26, 13–21.

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of rendering an oxide surface of an object resistant to the adhesion of a biopolymer, comprising treating an oxide surface of an object with a solution comprising a molecule that adheres to said surface, wherein said molecule comprises a biopolymer-resistant domain selected from the group consisting of oligoethers, oligoglycols, oligoalcohols, oligocarbonyls, oligosulfides, oligosulfones and oligosaccharides, thereby rendering said surface hydrophilic and biopolymer-resistant.

2. The method of claim 1, wherein said surface is designed to contact an aqueous solution comprising a biopolymer.

3. The method of claim 2, wherein said aqueous solution comprises a protein.

4. The method of claim 2, wherein said aqueous solution is blood.

5. The method of claim 1, wherein said surface is designed to contact a biological fluid.

6. The method of claim 1, wherein said object is designed to be implanted in the body of a manunal.

7. The method of claim 6, wherein said object is designed to be implanted in the body of a primate.

8. The method of claim 7, wherein said object is designed to be implanted in the body of a human.

9. The method of claim 1, 2, 3, 4, 5, 6, 7, or 8, wherein said molecule comprises a Z moiety, wherein Z is selected from the group consisting of —CO$_2$H, —PO$_3$H$_2$, —C(O)NHOH, —Si(OR)$_3$, —SiCl$_3$, —Sn(OR)$_3$, —SnCl$_3$, —Ge(OR)$_3$, and —GeCl$_3$, wherein R represents independently for each occurrence alkyl or acyl.

10. The method of claim 9, wherein said Z moiety adheres to said surface.

11. The method of claim 1, 2, 3, 4, 5, 6, 7, or 8, wherein Z is —Si(halide)$_3$, —Si(alkoxyl)$_3$ or —Si(acyloxy)$_3$.

12. The method of claim 1, wherein said biopolymer-resistant domain is selected from the group consisting of oligoethers, oligoglycols, and oligoalcohols.

13. The method of claim 9, wherein said molecule further comprises a W moiety, wherein W is H, a small alkyl group, an alkoxyl group, an acyl group, an acyloxy group, a sulfone, or a thioalkyl group.

14. The method of claim 13, comprising the further step of: treating said biopolymer-resistant surface of the object with a solution comprising a second molecule, wherein said second molecule adheres to said biopolymer-resistant surface of the object.

15. The method of claim 14, wherein said second molecule adheres to said biopolymer-resistant surface of the object via a coulombic interaction, a hydrophobic interaction, the formation of a covalent bond, or a combination thereof.

16. The method of claim 14, wherein the adherence of the second molecule to said biopolymer-resistant surface of the object modifies the biopolymer resistance of said surface.

17. The method of claim 16, wherein the adherence of the second molecule to said biopolymer-resistant surface of the object enhances the biopolymer resistance of said surface.

18. A method of rendering a surface of an object resistant to the adhesion of a biopolymer, comprising treating an oxide surface of an object with a solution comprising a molecule that adheres to said surface and renders said surface biopolymer-resistant, wherein said molecule is represented by general structure 1:

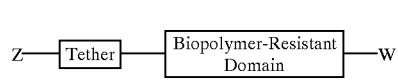

1 wherein

Z represents a domain, moiety, or functional group which associates with the surface of the object;

tether represents a covalent attachment between Z and the biopolymer-resistant domain;

biopolymer-resistant domain is selected from the group consisting of oligoethers, oligoglycols, oligoalcohols, oligocarbonyls, oligosulfides, oligosulfones and oligosaccharides; and W represents H, a small alkyl group, an alkoxyl group, an acyl group, an acyloxy group, a sulfone, or a thioalkyl group.

19. The method of claim 18, wherein:

Z is selected from the group consisting of —CO$_2$H, —PO$_3$H$_2$, —C(O)NHOH, —Si(OR)$_3$, —SiCl$_3$, —Sn(OR)$_3$, —SnCl$_3$, —Ge(OR)$_3$, and —GeCl$_3$, wherein R represents independently for each occurrence alkyl or acyl;

tether represents a hydrophobic covalent attachment, of approximately 5 to 20 bonds in length, between Z and the biopolymer-resistant domain; and biopolymer-resistant domain represents a molecular substructure selected from the set consisting of oligoethers, oligoglycols, oligoalcohols, oligocarbonyls, oligosulfides, oligosulfones, and oligosaccharides.

20. The method of claim 19, wherein:

Z represents —Si(OR)$_3$, —SiCl$_3$, —Sn(OR)$_3$, —SnCl$_3$, —Ge(OR)$_3$, or —GeCl$_3$.

21. The method of claim 20, wherein Z represents —Si(OR)$_3$ or —SiCl$_3$.

22. The method of claim 1 or 18, wherein said surface of said object comprises SiO$_2$.

23. A method of rendering a surface of an object resistant to the adhesion of a biopolymer, comprising treating a surface of an object with a solution comprising a molecule that adheres to said surface and forms an uncharged hydrophilic layer thereon, wherein said molecule comprises a biopolymer-resistant domain selected from the group consisting of oligoethers, oligoglycols, oligoalcohols, oligocarbonyls, oligosulfides, oligosulfones and oligosaccharides, thereby rendering the surface biopolymer-resistant, wherein the terminus of said adhered molecule that is exposed to the surroundings is H, a small alkyl group, an alkoxyl group, an acyl group, an acyloxy group, a sulfone, or a thioalkyl group.

24. The method of claim 23, wherein said surface is designed to contact an aqueous solution comprising a biopolymer.

25. The method of claim 24, wherein said aqueous solution comprises a protein.

26. The method of claim 24, wherein said aqueous solution is blood.

27. The method of claim 23, wherein said surface is designed to contact a biological fluid.

28. The method of claim 23, wherein said object is designed to be implanted in the body of a mammal.

29. The method of claim 28, wherein said object is designed to be implanted in the body of a primate.

30. The method of claim 29, wherein said object is designed to be implanted in the body of a human.

31. The method of claim 23, 24, 25, 26, 27, 28, 29, or 30, wherein said molecule comprises a Z moiety, wherein Z is selected from the group consisting of $—CO_2H$, $—PO_3H_2$, $—C(O)NHOH$, $—Si(OR)_3$, $—SiCl_3$, $—Sn(OR)_3$, $—SnCl_3$, $—Ge(OR)_3$, and $—GeCl_3$, wherein R represents independently for each occurrence alkyl or acyl.

32. The method of claim 31, wherein said Z moiety adheres to said surface.

33. The method of claim 23, 24, 25, 26, 27, 28, 29 or 30, wherein said molecule comprises a Z moiety, wherein Z is $—Si(halide)_3$, $—Si(alkoxyl)_3$ or $—Si(acyloxy)_3$.

34. The method of claim 31, wherein said molecule further comprises a biopolymer-resistant domain.

35. The method of claim 34, wherein said biopolymer-resistant domain is an oligoether, oligoglycol, oligoalcohol, oligocarbonyl, oligosulfide, oligosulfone or oligosaccharide domain.

36. The method of claim 31, wherein said molecule further comprises a W moiety, wherein W is H, a small alkyl group, an alkoxyl group, an acyl group, an acyloxy group, a sulfone, or a thioalkyl group.

37. The method of claim 36, further comprising treating said biopolymer-resistant surface of the object with a solution comprising a second molecule, wherein said second molecule adheres to said biopolymer-resistant surface of the object.

38. The method of claim 37, wherein said second molecule adheres to said biopolymer-resistant surface of the object via a coulombic interaction, a hydrophobic interaction, the formation of a covalent bond, or a combination thereof.

39. The method of claim 37, wherein the adherence of the second molecule on said biopolymer-resistant surface of the object modifies the biopolymer resistance of said surface.

40. The method of claim 39, wherein the adherence of the second molecule on said biopolymer-resistant surface of the object enhances the biopolymer resistance of said surface.

41. A method of rendering a surface of an object resistant to the adhesion of a biopolymer, comprising treating a surface of an object with a solution comprising a molecule that adheres to said surface and forms an uncharged hydrophilic layer thereon which renders the surface biopolymer-resistant, wherein said molecule is represented by general structure 1:

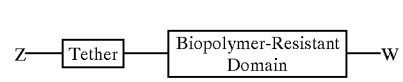

wherein

Z represents a domain, moiety, or functional group which associates with the surface of the object;

tether represents a covalent attachment between Z and the biopolymer-resistant domain;

biopolymer-resistant domain represents an uncharged molecular substructure selected from the group consisting of oligoethers, oligoglycols, oligoalcohols, oligocarbonyls, oligosulfides, oligosulfones and oligosaccharides; and W represents H, a small alkyl group, an alkoxyl group, an acyl group, an acyloxy group, a sulfone, or a thioalkyl group.

42. The method of claim 41, wherein:

Z is selected from the group consisting of $—CO_2H$, $—PO_3H_2$, $—C(O)NHOH$, $—Si(OR)_3$, $—SiCl_3$, $—Sn(OR)_3$, $—SnCl_3$, $—Ge(OR)_3$, and $—GeCl_3$, wherein R represents independently for each occurrence alkyl or acyl;

tether represents a hydrophobic covalent attachment, of approximately 5 to 20 bonds in length, between Z and the biopolymer-resistant domain; and biopolymer-resistant domain represents a molecular substructure selected from the set consisting of oligoethers, oligoglycols, oligoalcohols, oligocarbonyls, oligosulfides, oligosulfones, and oligosaccharides.

43. The method of claim 42, wherein:

Z represents $—Si(OR)_3$, $—SiCl_3$, $—Sn(OR)_3$, $—SnCl_3$, $—Ge(OR)_3$, or $—GeCl_3$.

44. The method of claim 43, wherein Z represents $—Si(OR)_3$ or $—SiCl_3$.

45. The method of claim 41, wherein said surface of said object comprises $SiO_2$.

46. The method of claim 18 or 41, wherein the biopolymer-resistant domain represents an oligoether.

47. The method of claim 46, wherein the oligoether comprises an oligo(ethylene glycol).

48. The method of claim 1 or 23, wherein the molecule is an oligoether-terminated alkyltrichlorosilane or an oligoether-terminated alkyltrialkoxysilane.

49. The method of claim 1 or 23, wherein the molecule is an oligo(ethylene glycol)-terminated alkyltrichlorosilane.

50. The method of claim 14 or 37, wherein the second molecule forms a covalent bond to said biopolymer-resistant surface.

* * * * *